US007375199B2

(12) United States Patent
Ohara et al.

(10) Patent No.: US 7,375,199 B2
(45) Date of Patent: May 20, 2008

(54) CANCER-ASSOCIATED GENES

(75) Inventors: Osamu Ohara, Chiba (JP); Takahiro Nagase, Chiba (JP); Daisuke Nakajima, Chiba (JP); Shin-ichi Funahashi, Ibaraki (JP)

(73) Assignees: Kazusa DNA Research Institute Foundation, Chiba (JP); Chugai Seiy Aku Kabushiki Kaisha, Tokyo (JP)

( * ) Notice: Subject to any disclaimer, the term of this patent is extended or adjusted under 35 U.S.C. 154(b) by 480 days.

(21) Appl. No.: 10/451,000

(22) PCT Filed: Dec. 21, 2001

(86) PCT No.: PCT/JP01/11305

§ 371 (c)(1),
(2), (4) Date: Sep. 8, 2003

(87) PCT Pub. No.: WO02/052008

PCT Pub. Date: Jul. 4, 2002

(65) Prior Publication Data

US 2005/0037347 A1   Feb. 17, 2005

(30) Foreign Application Priority Data

Dec. 22, 2000   (JP) ............... 2000-389742

(51) Int. Cl.
*C07H 21/02* (2006.01)
*C07H 21/04* (2006.01)
*C12P 21/06* (2006.01)
*C12N 5/00* (2006.01)

(52) U.S. Cl. ............ 536/23.1; 435/69.1; 435/325
(58) Field of Classification Search ............ 536/23.1
See application file for complete search history.

(56) References Cited

U.S. PATENT DOCUMENTS

2004/0048282 A1* 3/2004 Smolyar ............ 435/6

FOREIGN PATENT DOCUMENTS

| JP | 8-107797 A | 4/1996 |
| WO | WO 93/16178 A2 | 8/1993 |
| WO | WO 98/55643 A1 | 12/1998 |
| WO | WO 00/52044 A1 | 9/2000 |
| WO | WO 02/068579 A2 | 9/2002 |

OTHER PUBLICATIONS

Nagase et al., 7(DNA Res, vol. 7, p. 347-355, Dec. 31, 2000.*
Uniprot database, accession No. Q8CB10.*
Brennan FM, Chantry D, Jackson AM, Maini RN, Feldmann M. J Autoimmun. Jun. 1989; vol. 2 Suppl:177-86.*
Zimmer DB. Cell Motil Cytoskeleton. 1991;20(4):325-37.*
Powell et al., Parmacogenetics, 1998, vol. 8, p. 411-421.*
Carrere J, Guy-Crotte O, Gaia E, Figarella C. Apr. 1999; 44(4):545-51.*
Guo GL, Choudhuri S, Klaassen CD.J Pharmacol Exp Ther. Jan. 2002;300(1):206-12.*
Jang A and Hill RP. Clin Exp Metastasis. Sep. 1997;15(5):469-83.*
Hell et al., Laboratory Investigation, 1995, vol. 73, pp. 492-496.*
Auffray, Charles, et al. IMAGE: integration au niveau moleculaire de lanalyse du genome humain et de son expression, C.R. Acad. Sci. III, 1995, vol. 318, No. 2, pp. 263-272.
Auffray, Charles, et al. partial cDNA sequence, Fasta, Sep. 30, 1995, Accession Z44922.
Hillier, L., et al. yf97b01. r1 Soars infant brain 1N1B *Homo sapiens* cDNA clone, Fasta, Apr. 14, 1995, Accession R18623.
Database EMBL 'Online! *Homo sapiens* chromosome 15 clone RP11-64K12, retrieved from EBI Database accession No. ACO 13356—XP-002277568—Abstract.
Nagase et al., DNA Research, Universal Academy Press, JP, vol. 7, No. 6, pp. 347-355, (Dec. 31, 2000)—XP-001068355.
Database EMBL 'Online! *Homo sapiens* mRNA for KIAA1742 partial cds, retrieved from EBI Database accession No. ABO51529—XP-002277577—Abstract.
Walker et al., Genome Research, vol. 9, No. 12, pp. 1198-1203, (Dec. 1999)—XP-000872154.

* cited by examiner

*Primary Examiner*—Larry Helms
*Assistant Examiner*—Lei Yao
(74) *Attorney, Agent, or Firm*—Birch, Stewart, Kolasch & Birch, LLP

(57) ABSTRACT

The present invention is related to a DNA comprising a nucleotide sequence encoding a polypeptide represented by SEQ ID NO:1 or SEQ ID NO:2. The DNA according to the present invention is highly expressed in prostatic adenocarcinoma and ovarian carcinoma, and is a cancer-associated gene, so that it is possible to inhibit cancer by blocking the binding of the present protein to its ligand. Accordingly, the present antibody is used not only in the detection of the present protein, but also as an agent for the treatment or prevention of cancers such as prostatic adenocarcinoma and ovarian carcinoma.

7 Claims, 1 Drawing Sheet

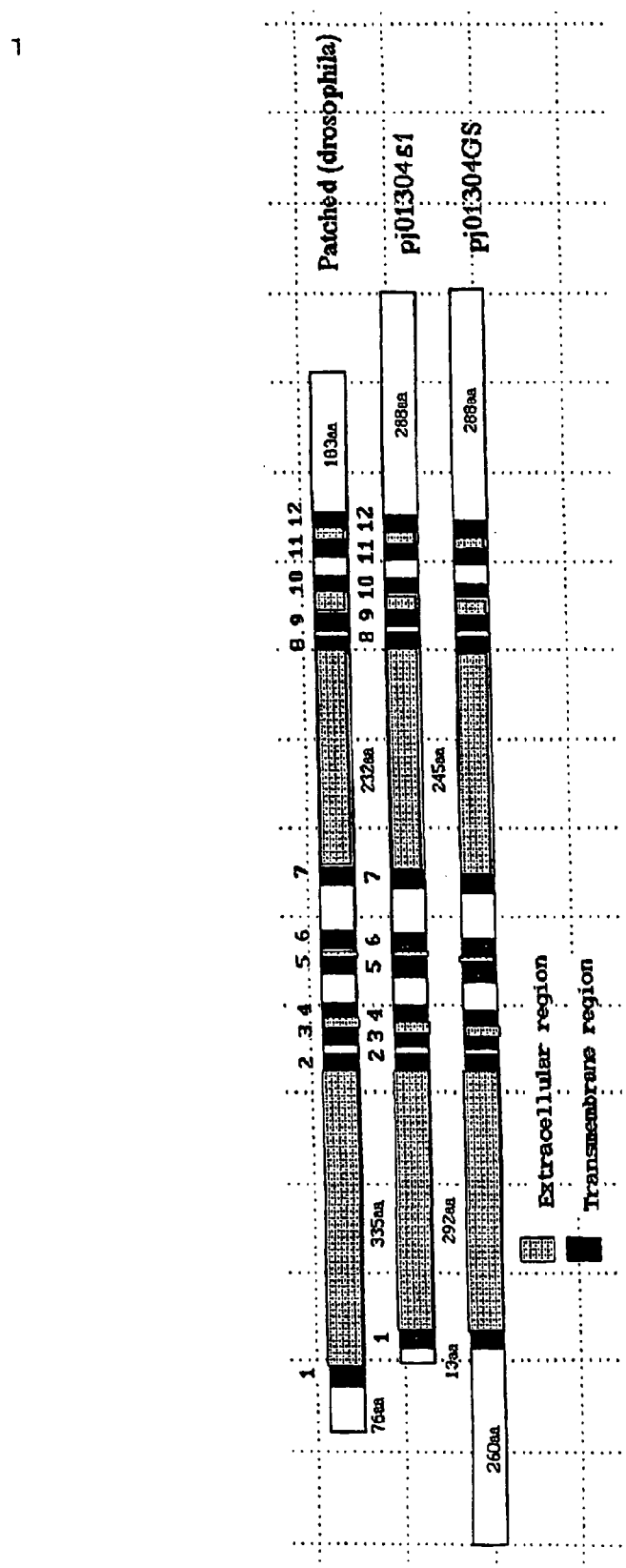

CANCER-ASSOCIATED GENES

This application is the national phase under 35 U.S.C. § 371 of PCT International Application No. PCT/JP01/11305 which has an International filing date of Dec. 21, 2001, which designated the United States of America.

FIELD OF THE INVENTION

The present invention is related to a novel DNA and a cancer-associated gene comprising the DNA, a recombinant protein encoded by the DNA, an antibody binding to the protein, an anti-cancer agent comprising the antibody, a method of screening a substance that binds to the protein or a peptide fragment thereof.

BACKGROUND OF THE INVENTION

A grand scale sequencing in the Human Genome Project has been producing a lot of information on the nucleotide sequences of human genome every day.

A final goal of the project is not only to determine the whole genomic nucleotide sequences, but also to reveal and understand various human life phenomena based on the information about their structure, i.e., DNA sequence information.

Regions encoding proteins occupy only a small part of the human genome. Although the coding region may recently be predicted by utilizing techniques in information technology such as neural network and hidden markov model, their predictive accuracy is not yet enough.

The present inventors have succeeded in directly cloning a novel DNA comprising a region encoding a protein from cDNA library derived from human adult whole brain, human amygdala, human adult hippocampus, and human fetal whole brain, and in determining its nucleotide sequence, and have completed the present invention.

SUMMARY OF THE INVENTION

A first aspect of the present invention relates to a DNA comprising a nucleotide sequence encoding the following polypeptide (a) or (b):
  (a) a polypeptide consisting of an amino acid sequence which is identical or substantially identical with an amino acid sequence represented by SEQ ID No. 1 or No. 2,
  (b) a polypeptide consisting of an amino acid sequence represented by SEQ ID No. 1 or No. 2 in which part of amino acids are deleted, substituted or added, and having substantially the same biological activity as the function of the polypeptide (a).

A second aspect of the present invention relates to a DNA of the following (a) or (b):
  (a) a DNA comprising a nucleotide sequence encoding an amino acid sequence represented by SEQ ID No. 1 or No. 2 in a nucleotide sequence represented by SEQ ID No. 1 or No. 2,
  (b) a DNA hybridizing with the DNA (a) under stringent conditions and encoding a protein having substantially the same biological activity as the function of the polypeptide consisting of the amino acid sequence in (a).

The DNAs of the first and second aspects will be also referred to as "the present DNA" in the present specification. The present invention also relates to the gene comprising the present DNAs.

A third aspect of the present invention relates to a protein comprising the following polypeptide (a) or (b):
  (a) a polypeptide consisting of an amino acid sequence which is identical or substantially identical with an amino acid sequence represented by SEQ ID No. 1 or No. 2,
  (b) a polypeptide consisting of an amino acid sequence represented by SEQ ID No. 1 or No. 2 in which part of amino acids are deleted, substituted or added, and having substantially the same biological activity as the function of the polypeptide (a), and to a recombinant protein which is obtained by the expression of the gene of the present invention.

A forth aspect of the present invention relates to various kinds of antibodies binding to the above protein.

A fifth aspect of the present invention relates to various kinds of anti-cancer agents comprising the above antibody.

A sixth aspect of the present invention relates to a method of screening a substance which binds to the above protein or a partial peptide thereof, comprising:
  (a) bringing a sample to be tested in contact with said protein or partial peptide thereof,
  (b) detecting a binding activity between the sample and said protein or partial peptide thereof, and
  (c) selecting a substance which has a binding activity to said protein or partial peptide thereof.

The seventh aspect of the present invention relates to a polynucleotide hybridizing with the DNA of Claim 1 or 2 under the stringent conditions and consisting of at least 15 bases.

The eighth aspect of the present invention relates to a method of detecting cancer with the use of the above polynucleotide as a probe, comprising:
  (a) bringing a sample to be tested in contact with said polynucleotide, and
  (b) detecting a hybridizing activity between the sample and said polynucleotide.

BRIEF DESCRIPTION OF THE DRAWINGS

FIG. 1 schematically shows the structures of the proteins of the present invention, "pj01304s1" and "pj01304GS", and Patched protein of *Drosophila*. A transmembrane region is painted in black, and an extracellular region is represented in thin dark. FIG. 1 shows the presence of two large extracellular domains.

BEST MODE FOR CARRYING OUT THE INVENTION

[DNA According to the Present Invention]

The present DNA is isolated as cDNA fragment from a cDNA library prepared by the present inventors by using as starting materials mRNAs of human adult whole brain, human amygdala, human adult hippocampus, and human fetal whole brain, are commercially available from Clontech, and identified with determination of its nucleotide sequence.

Thus, clones are randomly isolated from the library derived from human adult whole brain, human amygdala, human adult hippocampus, and human fetal whole brain, which is prepared in accordance with Ohara et al., DNA Research Vol.4, 53-59 (1997).

Next, after removing overlapped clones (clones which will repeatedly appear) with hybridization, the remaining clones are then subjected to transcription and translation in vitro and nucleotide sequences at both ends of clones which express a product with 50 kDa or more are determined.

Homology search is done on database to remove known genes with the use of the nucleotide sequences at both ends thus obtained as a query. The whole nucleotide sequence is determined for a clone which has identified as a novel gene.

In addition to the above screening method, the 3'- and 5'-terminal sequences are aligned with the human genome. And in the case an unknown long-ORF gene is found in a region caught between them, the whole length analysis of cDNA is done for the gene.

Unknown genes, which could not be obtained by conventional cloning techniques depending on known ones, can now be systematically cloned in this way.

Paying much attention not to make any artificial errors in short fragments or determined sequences, the whole region of human genes comprising the present DNA may be prepared by using PCR methods such as RACE.

A clone (KIAA1742) comprising the present DNA may be obtained accordingly. The function, etc. of a protein encoded by a gene in the clone is disclosed in the present specification.

The present DNA may be alternatively cloned by preparing a synthetic DNA primer with an appropriate nucleotide sequence such as a part of the polypeptide of the present invention, and amplifying it with an appropriate library by means of PCR. The present DNA may be further selected from DNAs integrated into appropriate vectors by means of hybridization with a DNA fragment or synthetic DNA encoding the whole region or part of the present polypeptide.

Hybridization may be performed in accordance with a method described in, for example, Current protocols in molecular biology (edited by Frederick M. Ausubel et al., 1987). If a commercial library is used it may be done according to a method described in instructions attached thereto.

The present DNA may be any DNA as long as it consists of a nucleotide sequence which encodes the polypeptide of the present invention, including a cDNA identified and isolated from cDNA libraries derived from human brain and other tissues or cells such as heart, lung, liver, spleen, kidney and testis, and a synthetic DNA.

A vector, which is used in the preparation of the libraries, includes bacteriophage, plasmid, cosmido and phagemid. The cDNA may be also amplified by means of Reverse Transcription coupled Polymerase Chain Reaction (RT-PCR) with the use of a total RNA or mRNA fraction prepared from the above tissues or cells.

An "amino acid sequence which is substantially identical with an amino acid sequence represented by SEQ ID No. 1 or No. 2" means an amino acid sequence having homology on an average of about 70% or more, preferably about 80% or more, more preferably about 90% or more, further more preferably about 95% or more to the whole amino acid sequence represented by SEQ ID No. 1 or No. 2.

Thus, the polypeptide consisting of the amino acid sequence which is substantially identical with the amino acid sequence represented by SEQ ID No. 1 or No. 2 includes a polypeptide having the above homology to the amino acid sequence represented by SEQ ID No. 1 or No. 2 and having substantially the same biological activity (or function) as the function of a polypeptide consisting of the above amino acid sequence. The term "substantially the same" means the activities or functions of the both substances are the same with each other in quality or property.

The present polypeptide includes a polypeptide consisting of the amino acid sequence represented by SEQ ID No. 1 or No. 2 in which part of amino acids (preferably 1~20, more preferably 1~10, further more preferably a few amino acids) are deleted, substituted or added, and having substantially the same biological activity (or function) as the function of the polypeptide consisting of the amino acid sequence represented by SEQ ID No. 1 or No. 2.

The DNA encoding the polypeptide consisting of the amino acid sequence which is substantially identical with the amino acid sequence represented by SEQ ID No. 1 or No. 2, or the polypeptide consisting of the amino acid sequence represented by SEQ ID No. 1 or No. 2 in which part of amino acids are deleted, substituted or added may be easily prepared by well known methods such as site-specific mutation, genetic homologous recombination, primer extension method and PCR, or any optional combinations thereof.

In order for the polypeptide or protein to have substantially the same biological activity, it is possible to make a substitution among amino acids belonging to the same group (polar, non-polar, hydrophobic, hydrophilic, positive-charged, negative-charged, or aromatic amino acid group) in the amino acids that constitute the present polypeptide. Alternatively, it is desirable to keep amino acids which are included in a functional domain.

Furthermore, the present DNA includes the DNA comprising a nucleotide sequence encoding the amino acid sequence represented by SEQ ID No. 1 or No. 2 in the nucleotide sequence represented by SEQ ID No. 1 or No. 2, and the DNA hybridizing with said DNA under stringent conditions and having substantially the same biological activity as the function of the polypeptide consisting of the amino acid sequence represented by SEQ ID No. 1 or No. 2.

The DNA that hybridizes with the DNA comprising the nucleotide sequence encoding the amino acid sequence represented by SEQ ID No. 1 or No. 2 in the nucleotide sequence represented by SEQ ID No. 1 or No. 2 under stringent conditions includes a DNA having homology on an average of about 80% or more, preferably about 90% or more, more preferably about 95% or more to the whole nucleotide sequence represented by SEQ ID No. 1 or No. 2.

Hybridization may be performed in accordance with a method described in, for example, Current protocols in molecular biology (edited by Frederick M. Ausubel et al., 1987). If a commercial library is used it may be done according to a method described in instructions attached thereto.

The phrase "stringent conditions" in this specification means conditions under which Southern blot hybridization is carried out in an aqueous solution containing 1 mM NaEDTA, 0.5M $Na_2HPO_4$ (pH 7.2) and 7% SDS at 65° C., followed by the washing of a membrane with an aqueous solution containing 1 mM NaEDTA, 40 mM $Na_2HPO_4$ (pH 7.2) and 1% SDS at 65° C.

The present DNA thus cloned may be directly used, or optionally digested with a restriction enzyme or tagged with a linker for use. The present DNA may have a translation initiation codon "ATG" at its 5'-end, and a translation termination codon, "TAA", "TGA" or "TAG" at its 3' end. These codons may be also added by using an appropriate synthetic DNA adapter.

[Polynucleotide According to the Present Invention]

Since the present DNA (gene) is highly expressed in cancer cells as seen from the following examples, detection of cancer can be done by detecting the gene according to the present invention.

Accordingly, the polynucleotide which hybridizes with the DNA comprising the nucleotide sequence represented by SEQ ID No. 1 or No. 2 under stringent conditions may be used as probe in the above detection of cancer.

The length of the polynucleotide is at least 15 bases, preferably 100 bases or more, more preferably 500 bases or more, further more preferably 1,000 bases or more.

The phrase "stringent conditions" in this specification means conditions under which Southern blot hybridization is carried out in an aqueous solution containing 1 mM NaEDTA, 0.5M $Na_2HPO_4$ (pH 7.2) and 7% SDS at 65° C., followed by the washing of a membrane with an aqueous solution containing 1 mM NaEDTA, 40 mM $Na_2HPO_4$ (pH 7.2) and 1% SDS at 65° C.

[Protein According to the Present Invention]

The protein according to the present invention may be easily prepared by any method known to those skilled in the art, by constructing an expression vector comprising the present DNA or the gene comprising thereof, culturing a transformant transformed with the expression vector to produce and accumulate the present polypeptide or a recombinant protein comprising thereof, and collecting them.

The expression vector may be constructed by any known method in the art. For example, it is made by (1) excising a DNA fragment containing the present DNA or the gene comprising the DNA, and (2) ligating the DNA fragment downstream of a promoter in the expression vector.

Vectors to be used in the present invention include those derived from *Escherichia coli* such as pBR322, pBR325, pUC18, pUC118; those derived from *Bacillus subtilis* such as pUB110, pTP5 and pC194; those derived from yeast such as pSH19 and pSH15; bacteriophage such as λphage; animal viruses such as retorovirus, vaccinia virus and baculovirus.

Promoters to be used in the present invention may be any promoters suitable for a host cell which is used in the expression of the gene, including, for example, trp promoter, lac promoter, recA promoter, λPL promoter and lpp promoter for *E. coli*; SPO1 promoter, SPO2 promoter and penP promoter for *Bacillus subtilis*; PHO5 promoter, PGK promoter, GAP promoter and ADH promoter for yeast; and SRα promoter, SV40 promoter, LTR promoter, CMV promoter and HSV-TK promoter for animal cells.

Other elements known in the art such as an enhancer, a splicing signal, a polyadenylation signal, a selection marker and SV40 replication origin may be added to the expression vectors. The protein encoded by the present DNA may be optionally expressed as a fused protein with other proteins such as glutathione-S-transferase and protein A. The fused protein may be cleaved by an appropriate protease and separated into each protein.

The host cell used in the present invention includes *Escherichia, Bacillus*, yeast, insect cells, and animal cells.

The examples of *Escherichia* include *E. coli* K-12·DH1 (Proc. Natl. Acad. Sci., USA, vol. 60 160 (1968)), JM103 (Nucleic Acids Research, vol. 9, 309 (1981)), JA221 (Journal of Molecular Biology, vol. 120, 517 (1978)) and HB101 (Journal of Molecular Biology, vol. 41, 459 (1969)).

The examples of *Bacillus* include *Bacillus subtilis* MI114 (Gene vol. 24, 255 (1983)), and 207-21(Journal of Molecular Biology, vol. 95, 87 (1984)).

The examples of yeast include *Saccaromyces cerevisiae* AH22, AH22R-, NA87-11A, DKD-5D, and 20B-12; *Schizosaccaromyces pombe* NCYC1913, NCYC2036; and *Saccaromyces picjia* pastoris.

The examples of animal cells include simian cell COS-7, Vero, Chinese hamster cell CHO ("CHO cell"), dhfr gene-defective CHO cell, mouse L cell, mouse AtT-20 cell, mouse myeloma cell, rat GH3 cell and human FL cell.

The transfomation of these cells may be carried out in accordance with a method known in the art such as those described in the following articles:

Proc. Natl. Acad. Sci., USA vol. 69, 2110 (1972); Gene, vol. 17, 107(1982), Molecular & General Genetics, vol. 168, 111 (1979); Methods in Enzymology, vol. 194, 182-187 (1991); Proc. Natl. Acad. Sci., USA vol. 75, 1929 (1978); Cell Engneering, additional volume 8, "New Cell Engineering experimental protocols, 263-267 (published by Shu-junn Co.); and Virology vol. 52 456 (1973).

The transformant thus transformed with the expression vector comprising the present DNA or the gene comprising thereof may be cultured according to a method known in the art.

*Escherichia* host cells may be normally cultured at about 15~43° C. for about 3~24 hours with aeration and stirring, if necessary. *Bacillus* host cells may be normally cultured at about 30~40° C. for about 6~24 hours with aeration and stirring, if necessary.

Yeast host cells may be normally cultured in a culture medium with pH about 5~8 at about 20~35° C. for about 24~72 hours with aeration and stirring, if necessary.

Animal host cells may be normally cultured in a culture medium with pH about 6~8 at about 30~40° C. for about 15~60 hours with aeration and stirring, if necessary.

The polypeptide or protein according to the present invention may be isolated and purified from the above culture as follows. After the completion of culturing, bacteria or cells are collected by a known method, suspended in an appropriate buffer solution, and destroyed by means of ultrasonic, lysozyme and/or freezing and thawing treatment, followed by centrifugation or filtration to give a crude protein extract. The buffer solution may contain a protein-denaturing agent such as urea and guanidine hydrochloride, or a surfactant such as TritonX-100™. If the protein is secreted into the culture medium, the bacteria or cells are separated from its supernatant by a known method after the completion of culturing, and the resulting supernatant is collected. The protein thus obtained and contained in the culture supernatant or extract may be purified by an appropriate combination of known separation and purification methods.

The present polypeptide or protein thus obtained may be converted into their salt form, which may be converted into its free from vice versa or into other salt forms according to a known method. The protein produced by the transformant may be treated with an appropriate protein-modifying enzyme such as trypsin or chymotrypsin in order to optionally add modification to it or to partially remove polypeptide from it before or after purification.

The presence of present polypeptide or protein or salt thereof may be determined by various binding assay methods or enzyme immunoassay using a specific antibody.

[Antibody According to the Present Invention]

There is no limitation in the present antibody as long as it binds to the protein according to the present invention. It may be obtained as a polyclonal antibody or monoclonal antibody by a known method. A preferable example of the present antibody is a monoclonal antibody derived from mammalian, which contains the one produced by a hybridoma and the one produced by a host cell which has been transformed by genetic engineering technique with an expression vector comprising a gene encoding the antibody. It is preferable that the present antibody specifically binds to the present protein.

The hybridoma producing the monoclonal antibody may be prepared with the use of a known technique. Thus, it is prepared by doing immunization with the present protein as a sensitizing antigen by a known method, fusing the resulting immunocyte with a known parent cell by a known cell fusion method, and screening a monoclonal antibody-producing cell by a known screening method. More specifically, the monoclonal antibody is prepared as follows.

A gene sequence encoding the present protein is inserted into a known expression vector system and an appropriate host cell is transformed with the vector, followed by purification of a desired protein from the host cell or a culture supernatant.

Next, the resulting protein is used as the sensitizing antigen. Alternatively, a partial polypeptide of the present protein, which may be usually obtained by a chemical synthesis method known to those skilled in the art based on the amino acid sequence of the present protein, is also used as the sensitizing antigen.

The partial polypeptide of the present protein includes those which have at least 10 amino acids or more, preferably at least 50 amino acids or more, more preferably at least 70 amino acids or more, further more preferably at least 100 amino acids or more, most preferably 200 amino acids or more of the amino acid sequence constituting the present protein, and the polypeptide have substantially the same biological activity with the function of the polypeptide according to the present invention. The partial polypeptide preferably comprises a functional domain, which will be described hereinafter. Although the C-end of the partial polypeptide is usually a carboxyl group (—COOH) or a carboxylate group (—COO—), it may be also an amide group (—CONH) or an ester group (—COOR) as it is for the present protein. The N-end of the partial polypeptide includes the one in which an amino group of methionine is protected with a protecting group, the one having a glutamyl group formed by cutting of the N-end in a body and subjected to pyroglutamic acid oxidation, the one in which a substituted group in the side chain of an amino acid is protected with an appropriate protecting group, and a complex peptide such as a glycopeptide in which a sugar chain is coupled.

The present antibody may be used in the detection and purification, etc. of the present protein. Since the present gene is expressed in a high degree in cancer cells as described in the Examples, the present antibody that is coupled with a radio isotope, a chemotherapeutic agent, toxins derived from bacteria can inhibit the growth of the cells. An epitope existing on the present protein, which can be recognized by the present antibody, is not limited to any particular one. Accordingly, any fragment may be used as the antigen in the preparation of the present antibody, as long as it comprises the epitope existing on the present protein.

The animal to be immunized with the sensitizing antigen is not limited to a particular one, but is usually selected in view of compatibility with the parent cell used in the cell fusion, including rodent such as mouse, rat and hamster.

The animal may be immunized with the sensitizing antigen by a known method, usually by intraperitoneal or subcutaneous injection. More specifically, the sensitizing antigen appropriately diluted and suspended in PBS (Phosphate-Buffered Saline) or physiological saline is appropriately mixed with a usual adjuvant such as Freund's complete adjuvant, emulsified and administered to the animal several times at an interval of 4-12 days. An appropriate carrier may be used in the immunization.

After the increase of an antibody level in serum of the immunized animal is confirmed, the immunocyte is collected and subjected to the cell fusion. A preferable immunocyte, for example, is a spleen cell.

The parent cell to be fused with the immunocyte is myeloma derived from mammalian, which includes various known cell strains such as P3 (P3x63Ag8.653)(J. Immunol. (1979) 123, 1548-1550), P3x63Ag8U.1(Current Topics in Microbiology and Immunology (1978) 81, 1-7), NS-1 (Kohler, G. and Milstein, C. Eur. J. Immunol. (1976) 6, 511-519), MPC-11 (Marguiles, D. H., et al., Cell (1976) 8, 405-415), SP2/0 (Shulman, M. et al., Nature (1978) 276, 269-270), FO (de St., Groth, S. F. et al., J. Immunol. Methods (1980) 35, 1-21), S194 (Trowbridge, I. S. J. Exp. Med. (1978) 148, 313-323), and R210 (Galfre, G. et al., Nature (1979) 277, 131-133).

The cell fusion between the immunocyte and myeloma may be done according to a known method such as that in Kohler, G. and Milstein, C. Methods Enzymol. (1981) 73, 3-46.

More specifically, the cell fusion is carried out in a usual nutritional medium in the presence of a cell fusion-promoting agent such as polyethyleneglycol (PEG) and Sendai virus (Hemagglutinating Virus of Japan: HVJ). An auxiliary agent such as dimethylsulfoxide may be optionally supplemented to increase hybridization efficiency.

A ratio of the amount of immunocyte to that of myeloma may be optionally selected, being preferably 1-10. Culture medium to be used in the cell fusion includes any culture medium which is used for culturing the above cells such as RPMI1640 culture medium and MEM culture medium. A serum-supplementing agent such as Fetal Calf Serum (FCS) may be used together.

Predetermined amounts of the immunocyte and the myeloma are mixed well in the above culture medium. PEG solution (e.g., with an average molecular weight of ca.1000-6000) warmed at about 37° C. in advance is added to a final concentration of 30-60% (w/v), and the cells are then mixed to form a desired hybridoma. After sequential addition of an appropriate culture medium, the process of centrifugation and removal of a supernatant is repeated in order to remove the cell fusion-promoting agent which is disadvantageous to the growth of the hybridoma.

The resulting hybridoma is then selected by being cultured in a usual selection medium such as HAT medium containing hypoxanthine, aminopterin and thymidine. The culture in HAT medium is maintained for enough of time (usually from several days to several weeks) so that non-fused cells (cells other than hybridoma) will die. Then, a hybridoma producing a desired antibody is screened and cloned with a limiting dilution method.

In addition to the immunization of the animal other than human with the antigen to obtain the hybridoma, it is possible to obtain a desired humanized antibody having a binding activity to the present protein by sensitizing human lymphocyte with the present protein in vitro and fusing the sensitized lymphocyte with human myeloma having immortality (Japanese Patent Publication Hei.1 (1989)-59878). Alternatively, a transgenic animal having the repertoire of all the genes for human antibody may be administered with the present protein to give a cell producing the present antibody, followed by the fusion of the resulting cell with an immortalized cell to produce the humanized antibody for the present protein PCT WO94/25585, WO93/12227, WO92/03918, WO94/02602).

The hybridoma thus prepared and producing the monoclonal antibody of the present invention may be maintained in passage culture using a usual medium, or may be stored in liquid nitrogen for a long period of time.

The monoclonal antibody may be obtained from the hybridoma by culturing the hybridoma in a usual method and collecting it from its supernatant, or by administering the hybridoma into its compatible mammalian and obtaining it from its ascites. The former method is suitable for the production of a highly purified antibody, and the latter method for a mass production of the antibody.

According to the present invention, a gene encoding an antibody is cloned from the hybridoma, inserted into an appropriate vector, introduced into the host cell and expressed by means of genetic recombination technique to give a recombinant-type monoclonal antibody (for example, Vandamme, A. M. et al., Eur. J. Biochem. (1990) 192, 767-775).

Specifically, mRNA encodng a variable (V) region of the present antibody is isolated from the hybridoma producing the present antibody, by preparing total mRNA with the use of guanidine-ultracentrifugation (Chirgwin, J. M. et al.Biochemstry (1979) 18, 5294-5299), AGPC method (Chomczynski, P. et al., Anal. Biochem. (1987) 162, 156-159) and the like, and preparing a desired mRNA with the use of mRNA Purification Kit (Pharmacia Co.). Alternatively, mRNA may be directly prepared by means of QuickPrep mRNA Purification Kit (Pharmacia Co.).

A cDNA of the variable (V) region of the present antibody is synthesized with the resulting mRNA by means of a reverse trascriptase. For example, the synthesis of cDNA may be done by using AMV Reverse Transcriptase First-strand cDNA Synthesis Kit (Seikagaku Industry Ltd.). Alternatively, the synthesis and amplification of cDNA may be done by using 5'-Ampli FINDER RACE Kit (Clontech Co.) and 5'-RACE method with PCR (Frohman, M. A. et al., Proc. Natl. Acad. Sci., USA (1988) 85, 8998-9002, Belyavsky, A. et al., Nucleic Acids Res. (1989) 17, 2919-2932), etc.

A desired DNA fragment is purified from the resulting PCR products and ligated with a vector DNA. The resulting expression vector is introduced into E. coli and the like. A colony containing a desired vector is selected and the vector is prepared from the colony. A nucleotide sequence of the desired DNA is confirmed by a known method such as dideoxy nucleotide chain termination method.

The desired DNA encoding the V region of the present antibody is then integrated into another expression vector containing a DNA encoding the constant region (C region) of a desired antibody.

The gene encoding the present antibody is integrated into an expression vector so that it will be expressed under a control of an expression-regulating region such as an enhancer and promoter. The host cell is then transformed with the expression vector to produce the antibody.

For the expression of the antibody, a DNA encoding a heavy chain (H chain) or a light chain (L chain) may be separately integrated into a different expression vector and used together for co-transformation of the host cell, or a DNA encoding both the H chain and L chain may be integrated into a single expression vector and used for transformation of the host cell (WO 94/11523).

Transgenic animals may be also used for the production of the recombinant-type antibody. For example, the gene for the antibody is inserted within a gene encoding a protein secreted specifically into milk (e.g., goat casein) to give a fused gene. A DNA fragment comprising the fused gene is injected into a goat's embryo, which is then introduced into a female goat. The desired antibody may be obtained from milk of transgenic goat which will be born by the goat having received the embryo or from milk of off-springs of the transgenic goat. Hormones may be optionally administered to the transgenic goat in order to increase an amount of milk comprising the desired antibody (Ebert, K. M. et al., Bio/Technology (1994) 12, 699-702).

In addition to the above antibodies, various genetic recombinant-type antibodies, which have been artificially modified in order to decrease heteroantigenecity against human, such as a chimera antibody and a humanized antibody may be used in the present invention.

The chimera antibody may be obtained by ligating the above DNA encoding the V region of the antibody with a DNA encoding the C region of a human antibody, integrating the resulting DNA into an expression vector, and introducing the vector into a host cell to produce it. The useful chimera antibody according to the present invention may be prepared according to these conventional methods.

The humanized antibody is also referred to as "reshaped humanized antibody", which is obtained by transplanting the CDR (complementary determining region) of an antibody from mammalian other than human, such as mouse into the CDR of a human antibody. A general technique of genetic recombination for the humanized antibody is also known (European Patent Application EP125023, WO96/02576).

Specifically, a DNA, which is designed so that it can ligate CDR of the mouse antibody with the framework (FR) region of the human antibody, is synthesized with the use of PCR by using as primer a few oligonucleotides having a part overlapping the end regions of both CDR and FR (WO98/13388).

The FR regions linked together through CDRs are selected so that the CDRs will constitute an excellent antigen-binding site. Amino acids in the FR of the V region of the antibody may be substituted, where necessary, so that the CDRs in the reshaped humanized antibody will form an appropriate antigen-binding site (Sato, K. et al., Cancer Res. (1993) 53, 851-856).

The C region in the chimera or humanized antibodies is derived from the human antibody, such as $C_H1$, $C_H2$, $C_H3$, and $C_H4$, for the H chain, and Cκ and Cλ for the L chain. The C region of the human antibody may be modified in order to improve stability of the antibody itself or the production thereof.

The chimera antibody consists of the variable region of antibodies derived from mammalian other than human and the constant region of the human antibody. On the other hand, the humanized antibody consists of the CDR of antibodies derived from mammalian other than human, and the FR region and the constant region of the human antibody. The humanized antibody is useful as an effective component in a therapeutic agent according to the present invention since antigenicity of the humanized antibody in human body is lowered.

The antibody used in the present invention may be a fragment of the antibody or a modified fragment thereof, including divalent and monovalent antibodies. For example, the fragment of the antibody includes Fab, F(ab')2, Fv, Fab/c having one Fab and a full Fc, and a single chain Fv (scFv) which is prepaerd by linking Fv of H chain and Fv of L chain via an appropriate linker. Specifically, an antibody is digested by an enzyme such as papain and pepsin to give the fragment of the antibody. Alternatively, genes encoding the above fragment are constructed and introduced into an expression vector, followed by the expression in a suitable host cell (Co, M. S. et al., J. Immunol. (1994) 152, 2968-2976, Better, M. & Horwitz, A. H. Methods in Enzymology (1989) 178, 476-496, Academic Press, Inc., Plueckthun, A. & Skerra, A. Methods in Enzymology (1989) 178, 476-496, Academic Press, Inc., Lamoyi, E., Methods in Enzymology (1989) 121, 652-663, Rousseaux, J. et al., Methods in Enzymology (1989) 121, 663-669, Bird, R. E. et al., TIBTECH (1991) 9, 132-137).

The scFv is prepared by linking Fv of H chain and Fv of L chain via an appropriate linker, preferably a peptide linker (Huston, J. S. et al., Proc. Natl. Acad. Sci. U.S.A. (1988) 85, 5879-5883). Each Fv of H chain and L chain may be derived from any antibody described in the present specification. The peptide linker used in the linking of V regions includes any single chain peptide having 12-19 amino acids.

A DNA encoding scFV may be prepared with the use of PCR in which amplification is done in the first step by using as template a DNA encoding all or a desired part of the amino acids in H chain or its V region and L chain or its V region and primers defining their both ends, and in the second step by using further a DNA encoding the peptide linker part and a pair of primers designed to ligate each end of the DNA with H chain and L chain, respectively.

Once the DNA encoding scFV is prepared, an expression vector comprising the DNA and a host cell transformed with the vector may be obtained according to a conventional method. The scFV may be produced with the use of the host cell by a conventional method as well.

The DNA encoding the above fragments of the antibody may be obtained, and these fragments of antibody may be expressed by the host cell as well. The "antibody" in the present invention includes these fragments.

As the modified antibody there may be mentioned those coupled with various molecules such as PEG. The antibody may be coupled with a radio isotope, a chemotherapeutic agent, a cytotoxic substance such as a bacteria toxin as well. The "antibody" in the present invention includes also these modified antibodies. These modified antibodies may be prepared by chemically modifying the resulting antibody by a conventional method.

The antibody used in the present invention also includes a bispecific antibody. The bispecific antibody may be the one having antigen-binding sites each of which recognizes a different epitope on the present protein, or the one having antigen-binding sites one of which recognizes an epitope on the present protein, and the other of which recognizes the chemotherapeutic agent or the cytotoxic substance such as a bacteria toxin. In the latter case, it is possible to directly apply the cytotoxic substance to a cell expressing the present protein (cancer cells) so that the cancer cells shall be specifically damaged and inhibited from growing. The bispecific antibody may be prepared by ligating a HL pair of two kinds of antibodies with each other, or by fusing hybridomas producing different monoclonal antibodies to give a hybridoma producing the bispecific antibody. Furthermore, the bispecific antibody may be prepared by genetic engineering technique.

The gene encoding the present antibody may be expressed and obtained by a known method. Where the mammalian cell is used, a conventionally used promoter, a gene for the antibody to be expressed and poly A signal 3'-downstream of the gene are functionally combined to express the gene. As a promoter/enhancer there may be mentioned human cytomegalovirus immediate early promoter/enhancer.

The other promoter/enhancers to be used in the present invention include promoter/enhancers derived from virus such as retrovirus, polyomavirus, adenovirus, and simian virus40 (SV40); and mammalian promoter/enhancer such as human elongation factor 1α (HEF1α).

SV40 promoter/enhancer and HEF1α promoter/enhancer may be used according to Mulligen, Nature (1979) 277, 108 and Mizushima et al., Nucleic Acids Res. (1990) 18, 5322, respectively, in order to easily express the gene.

A replication origin may be derived from SV40, polyoma virus, adenovirus, bovine papilloma vuirs (BPV), etc. The expression vector may further comprise a selection marker such as aminoglycoside transferase (APH) gene, thymidine kinase (TK) gene, E. coli xanthineguanine phosphoribosyl transferase (Ecogpt) gene, and dihydrofolic acid reductase (dhfr) in order to increase the number of copies of the gene in the host cell.

Where the E.coli is used, a conventionally used promoter, a signal sequence for secretion and a gene for the antibody to be expressed are functionally combined to express the gene. As a promoter/enhancer there may be mentioned lacz promoter and araB promoter, which are used according to Ward, Nature (1980) 341, 544-546; FASEB J. (1992) 6, 2422-2427, and Better, Science (1988) 240, 1041-1043, respectively.

A pelb signal sequence (Lei, S. P. et al., Bacteriol. (1987) 169, 4379) may be used for the production of the antibody in periplasma of E. coli. The antibody produced in the periplasma is separated and appropriately refolded for use.

The present antibody may be produced by any expression system such as eukaryotic and prokaryotic cell expression systems. The eukaryotic cell line includes established cells such as a mammalian cell, an insect cell, filamentous fungus, and yeast. The prokaryotic cell line includes bacteria cells such as E. coli. The antibody used in the present invention is preferably expressed in CHO, COS, myeloma, BHK, Vero, and Hela cells.

The transformed host cell is cultured in vitro or in vivo by a known method to produce the desired antibody. The culture medium includes DMEM, MEM, RPMI1640 and IMDM, which may be supplemented with a serum-supplementing agent such as fetal calf serum (FCS).

The thus expressed and produced antibody may be separated from the cell or host animal and purified to homogeneity. The separation and purification of the present antibody may be carried out with the use of an affinity column including Protein A column such as Hyper D, POROS, Sepharose F. F. (Pharmacia Co., etc.). Any other separation and purification methods which are used for usual proteins may be used. For example, the present antibody may be separated and purified with the use of a chromatography column other than the above affinity column, filter, ultra filtration, salting-out and dialysis, and any combination thereof (Antibodies A Laboratory Manual, Ed Harlow, David Lane, Cold Spring Harbor Laboratory, 1988).

Antigen-binding activity (Antibodies A Laboratory Manual, Ed Harlow, David Lane, Cold Spring Harbor Laboratory, 1988) and ligand receptor binding-inhibiting activity (Harada, A. et al., International Immunology (1993) 5, 681-690) may be determined by known methods.

The antigen-binding activity of the present antibody may be determined by ELISA (Enzyme Linked Immuno Sorbent Assay), EIA (Enzyme Immuno Assay), RIA (Radio Immuno Assay) and fluorescence antibody method. In the case of EIA, a sample containing the present antibody such as a culture supernatant of the cell producing the present antibody or a purified antibody is added to a plate coated with the present protein. After addition of a second antibody labeled with an enzyme such as alkaline phosphatase, the plate is incubated and washed. An enzyme substrate such as p-nitorophenyl phosphate is then added to the plate and absorbance is determined in order to evaluate the antigen-binding activity.

The present antibody may also have cytotoxicity activity such as complement-dependent cytotoxicity (CDC) activity and antibody-dependent cell-mediated cytotoxicity (ADCC) activity. The CDC activity in the present specification means cytotoxicity caused by a complement system, and the ADCC activity in the present specification means cytotoxicity caused by a cell having Fcγ receptor (e.g., immunocyte) which binds through its Fcγ receptor to the Fc portion of a specific antibody attached to a target cell.

The presence of CDC or ADCC activity of the present antibody may be determined by a known method (e.g., Current protocols in Immunology, Chapter 7. Immunologic studies in humans, Editor, John E., Coligan et al., John Wiley & Sons, Inc., (1993)).

Specifically, the cytotoxicity activity may be determined as follows:

Preparation of Effecter Cells

Spleen is extracted from CBA/N mouse and the like, and spleen cells are separated in RPMI1640 culture medium (GIBCO Co.). The cells are washed in the same medium containing 10% FBS (Hyclone Co.) and concentration of the cells is adjusted to $5 \times 10^6$/ml to give an effecter cell preparation.

Preparation of a Complement Solution

A complement solution is prepared by diluting Baby Rabbit Complement (CEDARLANE Co.,) ten times with the above medium containing 10% FBS (Hyclone Co.).

Preparation of Target Cells

The cells expressing the present protein (prostatic adenocarcinoma, ovarian carcinoma, colon adenocarcinoma, etc) are incubated with 0.2 mCi $^{51}$Cr-sodium chromate (Amersham Pharmacia Biotech Co.) in DMEM medium containing 10% FBS for one hour at 37° C. so as to be labeled with a radioisotope. After labeling with the radio isotope, the cells are washed three times with RPMI1640 medium containing 10% FBS and concentration of the cells is adjusted to $2 \times 10^5$/ml to give a target cell.

Determination of ADCC Activity

The present antibody (50 μl) and the target cell (50 μl) are added into a 96 U-well plate (Beckton Dickinson Co.) and reacted for 15 min. on ice. The effecter cell (100 μl) is then added and the resulting mixture is cultured for 4 hours in $CO_2$ incubator. The final concentration of the antibody is adjusted to 0 or 10 μg/ml. After the completion of the culture, 100 μl of supernatant is recovered and subjected to the determination of radioactivity by means of a gamma counter (COBRAIIAUTO-GMMA, MODEL D5005, Packard Instrument Company). The cytotoxicity (%) is calculated based on the formula: $(A-C)/(B-C) \times 100$ wherein "A" is the radio activity (cpm) of each test sample, "B" is the radio activity (cpm) of a sample mixed with 1% NP-40 (Nakarai Ltd.), and "C" is the radio activity (cpm) of a sample containing only the target cell.

Determination of CDC Activity

The present antibody (50 μl) and the target cell (50 μl) are added into a 96 U-well plate (Beckton Dickinson Co.) and reacted for 15 min. on ice. The complement solution (100 μl) is then added and the resulting mixture is cultured for 4 hours in $CO_2$ incubator. The final concentration of the antibody is adjusted to 0 or 3 μg/ml. After the completion of the culture, 100 μl of supernatant is recovered and subjected to the determination of radioactivity by means of the gamma counter. The cyotoxicity is determined by the same way as in ADCC activity.

[Anti-Cancer Agent According to the Present Invention]

An effective amount of administration of the anti-cancer agent of the present invention usually ranges from 0.00 mg~1,000 mg per 1 kg weight, or 0.01~100,000 mg/body of patient, being, however, not limited to these ranges. The present agent may be administered before or after the occurrence of clinical symptom. The present agent may be prepared according to a known method (Remington's Pharmaceutical Science, latest edition, Mark Publishing Company, Easton USA), while being optionally mixed together with pharmaceutically acceptable carriers or additives. These pharmaceutically acceptable carriers or additives include, for example, water, pharmaceutically acceptable organic solvent, collagen, polyvinylalcohol, polyvinylpyrrolidone, carboxylvinylpolymer, sodium carboxylmethylcellulose, sodium polyacrylate, sodium alginate, aqueous dextran, sodium carboxylmehylstarch, pectin, methylcellulose, ethylcellulose, xanthan gum, arabic gum, casein, agaraose, polyethylenglycol, diglycerine, glycerine, propylene glycol, petroleum jelly, paraffin, stearic alcohol, stearic acid, human serum albumin (HSA), mannitol, sorbitol, lactose, and pharmaceutically acceptable surfactant. The carries or additives may be optionally selected from the above-listed substances depending on a formulation type of the present agent. A preparation for injection may be a solution in solvent such as physiological saline, buffer solution and glucose solution supplemented with absorption-inhibiting agent such as Tween80, Tween20, gelatin, and HSA. A preparation of the present agent may be lyophilized and dissolved before use, including sugars or sugar alcohols such as mannitol and glucose as an excipient for lyophilization. The present agent is usually administered parentally, for example, by injection (subcutaneously, intravenouly, intramuscularly, intraperitoneally, etc.), percutaneously, permucously, administration through nose or lung, but may be administered orally as well.

[Method of Screening a Substance which Binds to the Above Protein or a Partial Peptide thereof]

The present protein is useful in screening of a substance which binds to it. Thus, it is used in a method of screening a substance which binds to the present protein, which comprises bringing a sample seemingly containing the substance in contact with said protein, detecting a binding activity between the sample and said protein and selecting a substance which has the binding activity.

The present protein used in the screening method may be a recombinant one, naturally occurring one, or a partial peptide thereof. Any material may be used as a sample of the method, including, for example, cell extracts, cell culture supernatants, products by fermenting bacteria, extracts from marine organisms, plant extracts, (crudely) purified proteins, peptides, non-peptide compounds, synthetic low molecular compounds, and natural compounds. The present protein to be brought in contact with the sample may be used as a purified one, a solubilized one, a complex with a carrier, a fused one with other proteins, an expressed one on a cell membrane, or a membrane component.

For example, a protein such as a ligand binding to the present protein may be screened with the use of any method known for those skilled in the art. These methods include Immunoprecipitation (Harlow, E. and Lane, D.: Antibodies, pp. 511-552, Cold Spring Harbor Laboratory publications, New York (1988)), West-Western blotting (Skolnik, E. Y. et al., Cell (1991) 65, 83-90), Two-hybrid system using cells (Fields, S., and Sternglantz, R., Trend. Genet. (1994) 10, 286-292, Dalton S, and Treisman R., (1992) Characterization of SAP-1, a protein recruited by serum response factor to the c-fos serum response element, Cell, 68, 597-612, [MATCHMAKER Two-Hybrid System][Mammalian MATCHMAKER Two-Hybrid Assay Kit][MATCHMAKER One-Hybrid System] (Clontech Co.), [HybriZAP Two-Hybrid Vector System] (Stratagene Co.), Affinitiy chromatography, and biosensor using surface plasmon resonance phenomenon.

The method for the separation of the compounds including protein, which bind to the present protein, includes known methods such as a screening method wherein the fixed present protein is reacted with a synthesized compound, a bank of natural materilas, and a random phage display library, and a molecular which can bind to the present protein is selected; and a screening method wherein a high through-put reaction is done by means of combinatorial chemistry technique (Wrighton N C; Farrell F X; Chang R; Kashyap A K; Barbone F P; Mulcahy L S; Johnson D L; Barrett R W; Jolliffe L K; Dower W J; Small peptides as potent mimetics of the protein hormone erythropoietin, Science (UNITED STATES) Jul. 26, 1996, 273 p458-464, Verdine G L., The combinatorial chemistry of nature, Nature (ENGLAND) Nov. 7, 1996, 384 p 11-13, Hogan J C Jr., Directed combinatorial chemistry, Nature (ENGLAND) Nov. 7, 1996, 384 p 17-17).

Since the compound which can be separated by the screening method according to the present invention may be a substance which inhibits the binding between the present protein and ligand, it will be utilized in an anti-cancer agent. Thus, the anti-cancer agent may be prepared by combining the compound separated by the present screening method with pharmaceutically acceptable carries.

[Others]

An antisense oligonucleotide (DNA) having a nucleotide sequence substantially complementary to a DNA encoding the present protein or a partial polypeptide thereof includes any antisense DNA as long as it has a nucleotide sequence substantially complementary to said DNA and has a function to inhibit the expression of the same DNA. The "nucleotide sequence substantially complementary" means, for example, that it has homology preferably of about 90% or more, more preferably of about 95% or more, most preferably of 100% to the whole or partial sequence of a nucleotide sequence complementary to the present DNA. Any nucleic acid sequence (a modified DNA or RNA) which shows a function similar to that of the antisense DNA is also included in the antisense DNA according to the present invention. These antisense DNAs may be prepared with a known DNA synthesizer.

The present DNA or gene comprising thereof may be used as a probe to detect abnormality in the DNA or its mRNA (genetic abnormality) encoding the present polypeptide or its partial peptide. They are therefore useful as a genetic diagnosis agent for detecting damage, mutation and under-expression of the DNA or mRNA; or for detecting increase and over-expression of the DNA or mRNA. The genetic diagnosis with use of the present DNA may be done by a known method such as Northern hybridization and PCR-SSCP (Genomics vol. 5, 874-879 (1989), Proceedings of the National Academy of Science of the United States of America, vol. 86, 2766-2770 (1989)).

The function of the protein according to the present invention can be effected in a patient in whom the present DNA or gene dose not normally function due to its abnormality, deletion or under-expression by a known method such as (1) the one in which the present DNA or gene is introduced into the patient and expressed by gene therapy with the use of an appropriate vector such as retrovirus vector, adenovirus vector and adenovirus-associated virus vector; and (2) the one in which they are injected into the patient.

The present DNA or gene may be also administered alone or in combination with an auxiliary to promote uptake by means of a gene gun or a catheter such as a hydrocatheter.

Single mutation in the present DNA or gene (cSNP), which is different from each individual, may be found by doing PCR of a chromosomal DNA extracted from human blood or tissue with the use of a synthetic DNA primer prepared based on the whole or partial nucleotide sequence of the present DNA or gene, and determining the nucleotide sequence of the PCR products. Individual constitution may be predicted by such cSNP, making possible to develop a drug suitable for each person.

Causal or responsible genes for human disorders may be searched and detected by isolating an orthologue (homo-logue or counterpart)) gene corresponding to the present DNA or gene in a model animal such as mouse, and making a model animal of the disorders with the use of knock out technique.

The abbreviation for a base and amino acid is shown in the present specification in accordance with IUPAC-IUB Commision on Biochemical Nomencalture or conventional methods, and an optical isomer of the amino acid, if any, means its L-isomer unless otherwise instructed.

EXAMPLES

The present invention will by further explained by the following examples, which do not limit the scope of the present invention. The genetic procedures in the examples are done in accordance with those described in Current protocols in molecular biology (edited by Frederick M. Ausubel et al., 1987).

(1) Construction of cDNA Library Derived from Human Adult Whole Brain, Human Amygdala, Human Adult Hippocampus, and Human Fetal Whole Brain A double-stranded cDNA was synthesized by SuperScript II reverse transcriptase kit (Invitrogen Co.) with the use of an oligonucleotide having NotI site (GACTAGTTCTA-GATCGCGAGCGGCCGCCC(T)$_{15}$) (SEQ ID NO: 3) (Invitrogen Co.) as a primer, and mRNA derived from human adult whole brain, human amygdala, human adult hippocampus, and human fetal whole brain (Clontech Co.) as a template. An adapter having SalI site (Invitrogen Co.) was ligated with the resulting cDNAs. After digestion with NotI, the cDNAs were subjected to electrophoresis on a low-melting agarose of 1% to purify cDNA fragments with 3 kb or more.

The thus purified cDNA fragments were ligated with pBluescript II SK+plasmid treated with SalI-NotI restriction enzymes. The resulting recombinant plasmids were introduced into *E.coli* DH10B strain (Invitrogen Co.) by an electroporation method.

(2) Screening (No. 1)

Clones were randomly picked up from the thus constructed cDNA library and spotted on a membrane. A mixture of oligoDNAs (21 base-long each) prepared on the basis of the nucleotide sequences of about 1,300 clones which had been analyzed about their whole nucleotide sequences were labeled with DIG by terminal transferase at their 3'-ends. Overlapping clones which will appear repeatedly were then removed by dot hybridization with use of the mixture of the above labeled oligoDNAs as a probe (Current protocols in molecular biology (edited by Frederick M. Ausubel et al., 1987).

After the transcription and translation system in vitro (Promega Co., TNT T7 Quick Coupled Transcription/Translation System cat. no. L1107), clones expressing products with 50 kDa or more were selected.

The terminal nucleotide sequences of the selected clones were determined, and the homology search was done on nr database (all GenBank+EMBL+DDBJ+PDB sequences, but no EST, STS, GSS or phase 0.1 or 2 HTGS seqeunces) with the use of the resulting sequences as a query in accordance with homology search program BLASTN2.2.1 (Altshul, Stephen F., Thomas L. Madden, Alejandro A., Schaffer, Jinghui Zhang, Zheng Zhang, Webb Miller, and David J. Lipman (1997), "Gapped BLAST and PSI-BLAST: a new generation of protein search programs.", Nucleic acids Res. 25:3389-3402). As a result, a gene having no homologous gene, i.e., a novel gene, is subjected to the whole nucleotide sequence analysis.

Screening (No. 2)

The terminal sequences of 3'- and 5'-ends of the above cDNAs were aligned with human genomic sequence (ncbi.nlm.nih.gov/genomes/H_sapiens/) with the use of homology search program BLASTN2.2.1.

Genes were picked up from a genome region inserted between them by the use of Genscan program (computer software for predicting a gene from genome sequences) (Burge, C. and Karlin, S. 1987, Prediction of complete gene structures in human genomic DNA, J. Mol. Biol., 268, 78-94). Homology search was done on mergedb, which had been prepared by combining human cDNA sequences determined by KAZUSA DNA Institute and Homo sapiens database of GenBank (except EST and genome) without overlapping data, with the use of the selected genes as a query in accordance with homology search program BLASTN2.1.3. When a novel long-ORF gene (with 1,200 bp or more of cds according to the prediction by Genscan) was found, the full-length sequences of its 5'- and 3'-ends were determined.

Determination of the nucleotide sequence was carried out by means of a DNA sequencer (ABI PRISM377) and a reaction kit manufactured by PE Applied Bio System Co. Most of the sequences were determined by a diterminator method on shotgun clones, and parts of them were determined by a primer-walking method with the use of oligonucleotides that were synthesized based on the thus determined nucleotide sequences.

The novel DNAs or genes were screened in the above ways. As a result, a done pj01304 was found. Furthermore, the 3'- and 5'-end sequences of about 100,000 clones isolated from brain cDNA library prepared by Ohara et al. and about 2,000 full-length clones were assembled together, and grouping of cDNA clones derived from the same gene was done.

As a result, a clone pj05443 comprising an upstream region of the clone pj01304 was finally found in a group containing the clone pj01304.

The upstream region of the clone pj01304 was then excised from the clone pj05443 and ligated with the clone pj01304 to give a clone pj01304s1 (KIAA1742) comprising the novel DNA or gene represented in SEQ ID NO. 1 or NO. 2 according to the present invention. The nucleotide sequence from 1 bp to 820 bp of the clone pj01304s1 is derived from the clone hj05443, and that from 821 bp to 5,035 bp is derived from the clone pj01304.

(3) Expression of the Protein Encoded by the Present Gene

A gene product was expressed from the cDNA clone pj01304 with the use of the transcription and translation system in vitro (Promega Co., TNT T7 Quick Coupled Transcription/Translation System cat. no. L1107).

The product incorporated with $^{35}$S-labeled methionine was subjected to SDS-PAGE (12.5%). After drying of a gel, autoradiography was done with the use of BAS2000 (Fuji film) system to detect the gene product of the clone pj01304. As a result, a band, which was presumed to be a transcription/translation product of the done pj01304, was observed at a point corresponding to a marker with 135 kDa.

As a molecular weight of the protein encoded by the pj01304 consisting of 1,137 amino acids from a first methionine is presumed to be about 124 kDa, the presumed molecular weight was coincided well with the above result.

(4) Homology Research of the Present DNA

The homology search of the whole nucleotide sequence thus determined was done on the known nr data in accordance with homology search program BLASTN2.2.1 (Altshul, Stephen F., Thomas L. Madden, Alejandro A., Schaffer, Jinghui Zhang, Zheng Zhang, Webb Miller, and David J. Lipman (1997), "Gapped BLAST and PSI-BLAST: a new generation of protein search programs.", Nucleic acids Res. 25:3389-3402). As a result, the present DNA has homology to a gene shown in Table 1. Table 1 shows information about the gene (homologous gene) such as its name, data base ID, species, length of protein, etc. The meaning of each item in Table 1 is as follows:

"Homologous region, clone": the starting and ending points of the homologous region in the present clone;

"Homologous region, homologous gene": the starting and ending points of the homologous region in the homologous gene;

"Score": the higher this value is, the higher credibility is;

"E-value": the closer this value comes to "0", the higher credibility become;

"Homology": the percentage of identical amino acids in the homologous region; and "Percentage of the homology region": the percentage of the homologous region in the homologous gene.

TABLE 1

| Homologous region | | | | Homology Value | | | Percentage of the homology region |
|---|---|---|---|---|---|---|---|
| Clone | | Homologus gene | | | | | |
| from | to | from | to | Score | E-value | Homology | |
| 59 | 913 | 236 | 1125 | 423 | e–117 | 31%(287/923) | 73% |

| Homologous gene | | | | |
|---|---|---|---|---|
| Name | Data base | Species | Length of protein | Publication |
| CG2019 | gb|AAF51938.1l | Dm | 1218 | — |

(5) Search of Domains

The DNA according to the present invention (KIAA1742) is a gene with 5,035 bp encoding a protein with 1,245 amino acids. Motif search by the use of HMMER2.1.1 (S. R. Eddy. Profile hidden Markov models. Bioinfomatics 14:755-763, 1998) revealed the existence of a motif of Patched family which is involved in a signal of hedgehog-smoothend in the region of amino acids No. 145-954.

Further, the search with the use of Sosui (Bioinformatics (1998) May; 14(4):378-379) predicted the presence of 12 transmembrane regions as shown in Table2. It was assumed that the region of amino acids No. 39-328 (a region between the first and second transmembrane regions) and the region of amino acids No. 560-802 (a region between the seventh and eighth transmembrane regions) constituted a large loop, which was very similar to the structure of Patched (Cell 59, 751(1989); Cancer Letter (2001) 173, 1-7) as shown in FIG. 1.

TABLE 2; SEQ ID NOS: 6-17, in order from top to bottom, respectively.

TABLE 2

| No | N terminal | transmembrane region | C terminal | length |
|----|------------|----------------------|------------|--------|
| 1  | 14         | VAVLMLCLAVIFLCTLAGLLGARLP | 38     | 25     |
| 2  | 329        | LVQDTVYPLLALVAIFFGMALYLRS | 353    | 25     |
| 3  | 357        | TLMVLLGVLGSLLVAFFLYQVAFRM | 381    | 25     |
| 4  | 385        | PFVNLAALLLLSSVCANHTLIFFDL | 409    | 25     |
| 5  | 433        | FGYLLLVSGLTTSAAFYASYLSRLP | 457    | 25     |
| 6  | 463        | ALFMGTAVLVHLALTLVWLPASAVL | 487    | 25     |
| 7  | 535        | FQRLLPCGVIKFRYIWICWFAALAA | 559    | 25     |
| 8  | 803        | SLSTEPAVVLGLALALAFATLLLGT | 827    | 25     |
| 9  | 831        | PLSLFSVAAVAGTVLLTVGLLVLLE | 855    | 25     |
| 10 | 864        | LFLSASVGLSVDFTVNYCISYHLCP | 888    | 25     |
| 11 | 902        | QTSCATAVGAAALFAAGVLMLPATV | 926    | 25     |
| 12 | 934        | IILMMVKCVSCGFASFFFQSLCCFF | 958    | 25     |

Brief Explanation of Table 2

The amino acid sequences and locations of the predicted 12 transmembrane regions are shown in Table 2. "N terminal" and "C-terminal" show the number of the amino acid at N-terminal and C-terminal, respectively. "Length" means the length of transmembrane region.

"Patched" was found in Drosophia as a protein having 12 transmembrane regions, which functions as a tumor suppressor of blocking a signal of Smoothend. Patched has two large hydrophllic and extracellular loops, and transmits the signal through direct or indirect interaction with Smoothend. However, it is assumed that the binding of Hedgehog will release the blocking of the signal of Smoothend and cause basal cell carcinoma. Patched is known to control the transcription of members of TGFβ such as BMP or Wnt families (EMBO J (1998) 17, 3505-3511), Cancer Letter (2001) 173, 1-7). It has been reported that Hptc (Human gene homologue to ptc) is involved in skin carcinoma (Am J Pathol (2001) 158, 381-385, PNAS (1999) 96, 5117-5122).

The present protein belonging to Patched family has homology of 31% to Dispatched of the same family, and it is the protein having 12 transmembrane regions like Patched. Gene expression profiling showed that increase of the expression of the present gene was observed in prostatic adenocarcinoma and ovarian carcinoma in, it is assumed that the present gene acts as an oncogene, but not as a tumor suppressor gene like Patched. It is conceived that the present protein will interact with Smoothend or other proteins through the two large extracellular loops and transmit cancer signal. Or it may competitively act against the binding between Hedgehog and Patched, and transmit cancer signal.

In view of the above knowledge and information about the biological activity (function) of the present DNA, it is considered that the present DNA is a cancer-associated gene, and that it is possible to inhibit cancer by blocking the binding of the present protein to its ligand.

Accordingly, the present antibody is used not only in the detection of the present protein, but also as an agent for the treatment or prevention of cancers such as prostatic adenocarcinoma and ovarian carcinoma (6) Real-Time PCR Analysis of the Transcription Products An amount of the transcription product of the present gene were analyzed by using cDNA in each tissue with ABI PRISM® 7700 Sequence Detection System (ABI Co.) The expression amount of GAPDH gene was analyzed with Pre-Developed TaqMan PCR Assay Kit (ABI Co. #4310884E). Master Mix was prepared by mixing 1.25 µl of 20×Control Mix (GAPDH), 6.25 µl of DEPC-treated water (Ambion Co. #9920) and 12.5 µl of TaqMan Universal PCR Master Mix (ABI Co. #4304437). After the addition of 5 µl of MTC Panel cDNA (Clontech Co.) to the Master Mix to a final volume of 25 µl, gene amplification was done by 2 min. at 50° C., 10 min. at 95° C., and repeating 40 cycles of 15 sec. at 95° C. and 1 min. at 60° C. on MicroAmp Optical 96-wel Reaction Plate (ABI Co. #N801-0560). Human MTC™ Panel I (K1420-1), Human MTC™ Panel II (K1421-1) and Tumor MTC™ Panel I (K1422-1) were used as MTC Panel cDNA.

An expression amount of the present gene was analyzed by amplification with the use of a primer 1742-3538 (5'-CAGCACTCACACGTCAGGCT-3') (SEQ ID NO: 4), and a primer 1742-3658 (5'-AGAAATACCTTCGGGCTCCAG-3') (SEQ ID NO: 5). O.5. of the primer 1742-3538 (10 µM), 0.5 µl of the primer 1742-3658 (10µM), 6.5µl of DEPC-treated water, 12.5 µl of SYBR Green PCR Master Mix (ABI Co. #4309155) were mixed together to a final volume of 20 µl, followed by the addition of 1 µl of MTC Panel cDNA (Clontech Co.) and 4 µl of DEPC-treated water to a final volume of 25 µl. Gene amplification was done by 2 min. at 50° C., 10 min. at 95° C., and repeating 40 cycles of 20sec. at 95° C., 30sec. at 59° C., and 30sec. at 72° C. on MicroAmp Optical 96-well Reaction Plate (ABI Co. #N801-0560) with the use of ABI PRISM® 7700 Sequence Detection System (ABI Co.). Relative values were calculated based on a standard curve of control cDNA attached to MTC Panel with the use of the expression amount of GAPDH gene GAPDHgene as a standard control. A vector comprising the present gene cloned in pBluescript (40 pg/µl) was serially diluted 5 times and the resulting solutions were then used as reference. The relative values in each tissue obtained by dividing the expression amount of the present gene by that of GAPDH gene are summarized and compared among one another in Table 3.

In Table 3, figures in the right column indicate the expression amount of the KIAA1742 gene, which was normalized with the expression amount of GAPDH gene in each tissue, and shown as a relative value against prostate of value "1".

Table 3 clearly shows that the high values are obtained in prostatic adenocarcinoma and ovarian carcinoma.

TABLE 3

| Tissue | KIAA1742/GAPDH |
| --- | --- |
| Heart | 0.28 |
| Brain | 36.60 |
| Placenta | 1.97 |
| Lung | 1.78 |
| Liver | 3.85 |
| skeletal muscle | 0.06 |
| Kidney | 0.57 |
| Pancreas | 3.60 |
| Spleen | 2.57 |
| Thymus | 0.48 |
| Prostate | 1.00 |
| Testis | 5.87 |
| Ovary | 1.10 |
| small intestine | 6.81 |
| Colon | 13.03 |
| peripheral blood leukocyte | 0.27 |
| breast carcinoma GI-101 | 0.61 |
| lung carcinoma LX-1 | 0.46 |
| colon adenocarcinoma CX-1 | 8.87 |
| lung carcinoma GI-117 | 0.12 |
| prostatic adenocarcinoma PC3 | 229.78 |
| colon adenocarcinoma GI-112 | 0.99 |
| ovarian carcinoma | 28.36 |
| pancreatic adenocarcinoma GI-103 | 0.87 |

(7) Location on Chromosome

It was further confirmed that the present gene was expressed in cerebellum with the use of PT-PCR Coupled ELISA. Alignment of the DNA sequence of the present clone with a human genomic library (ncbi.nlm.nih.gov/genomes/H_sapiens/) showed that the present gene was located on chromosome 15.

(8) Preparation of pj01304s1(KIAA1742) Gene Family

Homology search of the DNA sequence of the pj01034s1 gene was done on human genomic sequences (ftp://ncbi.nlm.nih. gov/genomes/H_sapiens/) in accordance with BLSTN2.2.1 hit a particular genomic fragment (GenBank ID NT_010194.6).

The pj01304GS gene, which has a high homology to the pj01304s1 gene (100% at DNA level and 100% at protein level; aligned by GenWorks (Intelligenetics Co.)), was then found with the use of Genscan program (Burge, C. and Karlin, S. 1987, Prediction of complete gene structures in human genomic DNA, J. Mol. Biol., 268, 78-94: computer software for predicting a gene from genome sequences). The pj01304GS gene has 4,479 bp, which encodes a protein having 1,492 amino acids. Its nucleotide sequence and amino acid sequence are shown as SEQ ID NO. 2.

The alignment between the pj01304GS gene and the pj01304s1 gene is shown in Table 4. As seen from Table 4, an amino acid sequence of No. 248-1,492 encoded by the pj01304GS gene is identical with an amino acid sequence of No. 1-1,245 encoded by the pj01304s1 gene, showing that the pj01304GS gene has a nucleotide sequence encoding an amino acid sequence of No. 1-247 located 5' upstream of the pj01304s1 gene. Accordingly, it is considered that both the genes are generated from the same genome by an alternative splicing. It is also considered that as the pj01304GS gene has the same domains as the pj01304s1 gene, it will show similar activities. Thus, the pj01304GS gene and protein encoded thereby are included in the DNA and protein according to the present invention, respectively.

Those skilled in the art may easily prepare those genes by, for example, RT-PCR. Thus, PCR is done by the use of an upstream primer (5'-ATGGGAAGAAAGACCCAACC-3': 1~20 bp of the SEQ ID NO. 2) and a downstream primer (5'-CAAGTCCTGGCAGGGAACTG-3': 588~607 bp of the SEQ ID NO. 2), and cDNA as a template obtained by reverse transcription from human adult cerebellum mRNA with random primers. The resulting DNA is then ligated with the pj01304s1 gene by known methods such as Chuan Li et al., Ligation independent cloning irrespective of restriction site compatibility, Nucleic Acids Res. 1997 25:20 (4165-4166) to give a clone encoding the pj01304GS protein.

Alignment of pj0130405 (SEQ ID. NO:2) with pj01304s1 (SEQ ID NO:1) showing consensus sequence (SEQ ID NO:2).

TABLE 4

| pj01304GS | MGRKTQPDAS PHWGGEEGAE RAGNLAGLKP PASTRGVQRG EVRAWSSPSI | 50 |
| --- | --- | --- |
| pj01304s1 | - - - - - - - - - - - - - - - - - - - - - - - - - - - - - - - - - - - - - - - - - - - - - - - - - - - | 50 |
| Consensus | . . . . . . . . . . . . . . . . . . . . . . . . . . . . . . . . . . . . . . . . . . . . . . . . . . . | |

| pj01304GS | RLEGAYACAR APRRRCRRHR RRRRRRRGFS TSARTAVPPT GMGDSSSSS | 100 |
| --- | --- | --- |
| pj01304s1 | - - - - - - - - - - - - - - - - - - - - - - - - - - - - - - - - - - - - - - - - - - - - - - - - - - | 100 |
| Consensus | . . . . . . . . . . . . . . . . . . . . . . . . . . . . . . . . . . . . . . . . . . . . . . . . . . | |

| pj01304GS | GGSGPAPGPG PEGEQRPEGE PLAPDGGSPD STQTKAVPPE ASPERSCSLH | 150 |
| --- | --- | --- |
| pj01304s1 | - - - - - - - - - - - - - - - - - - - - - - - - - - - - - - - - - - - - - - - - - - - - - - - - - - | 150 |
| Consensus | . . . . . . . . . . . . . . . . . . . . . . . . . . . . . . . . . . . . . . . . . . . . . . . . . . | |

| pj01304GS | SCPLEDPSSS SGPPPTTSTL QPVGPSSPLA PAHFTYPRAL QEYQGGSSLP | 200 |
| --- | --- | --- |
| pj01304s1 | - - - - - - - - - - - - - - - - - - - - - - - - - - - - - - - - - - - - - - - - - - - - - - - - - - | 200 |
| Consensus | . . . . . . . . . . . . . . . . . . . . . . . . . . . . . . . . . . . . . . . . . . . . . . . . . . | |

| pj01304GS | GLGDRAALCS HGSSLSPSPA PSQRDGTWKP PAVQHHVVSV RQERAFQMPK | 250 |
| --- | --- | --- |
| pj01304s1 | - - - - - - - - - - - - - - - - - - - - - - - - - - - - - - - - - - - - - - - - - - - - - - MPK | 3 |
| Consensus | . . . . . . . . . . . . . . . . . . . . . . . . . . . . . . . . . . . . . . . . . . . . . . . . MPK | 250 |

TABLE 4-continued

| | | |
|---|---|---|
| pj01304GS | SYSQLIAEWP VAVLMLCLAV IFLCTLAGLL GARLPDFSKP LLGFEPRDTD | 300 |
| pj01304s1 | SYSQLIAEWP VAVLMLCLAV IFLCTLAGLL GARLPDFSKP LLGFEPRDTD | 53 |
| Consensus | SYSQLIAEWP VAVLMLCLAV IFLCTLAGLL GARLPDESKP LLGFEPRVTD | 300 |
| | | |
| pj01304GS | IGSKLVVWRA LQALTGPRKL LFLSPDLELN SSSSHNTLRP APRGSAQESA | 350 |
| pj01304s1 | IGSKLVVWRA LQALTGPRKL LFLSPDLELN SSSSHNTLRP APRGSAQESA | 103 |
| Consensus | IGSKLVVWRA LQALTGPRKL LFLSPDLELN SSSSHNTLRP APRGSAQESA | 350 |
| | | |
| pj01304GS | VRPRRMVEPL EDRRQENFFC GPPEKSYAKL VFMSTSSGSL WNLHAIHSMC | 400 |
| pj01304s1 | VRPRRMVEPL EDRRQENFFC GPPEKSYAKL VFMSTSSGSL WNLHAIHSMC | 153 |
| Consensus | VRPRRMVEPL EDRRQENFFC GPPEKSYAKL VFMSTSSGSL WNLHAIHSMC | 400 |
| | | |
| pj01304GS | RMEQDQIRSH TSFGALCQRT AANQCCPSWS LGNYLAVLSN RSSCLDTTQA | 450 |
| pj01304s1 | RMEQDQIRSH TSFGALCQRT AANQCCPSWS LGNYLAVLSN RSSCLDTTQA | 203 |
| Consensus | RMEQDQIRSH TSEGALCQRT AANQCCPSWS LGNYLAVLSN RSSCLDTTQA | 450 |
| | | |
| pj01304GS | DAARTLALLR TCALYYHSGA LVPSCLGPGQ NKSPRCAQVP TKCSQSSAIY | 500 |
| pj01304s1 | DAARTLALLR TCALYYHSGA LVPSCLGPGQ NKSPRCAQVP TKCSQSSAIY | 253 |
| Consensus | DAARTLALLR TCALYYHSGA LVPSCLGPGQ NKSPRCAQVP TKCSQSSAIY | 500 |
| | | |
| pj01304GS | QLLHFLLDRD FLSPQTTDYQ VPSLKYSLLF LPTPKGASLM DIYLDRLATP | 550 |
| pj01304s1 | QLLHFLLDRD FLSPQTTDYQ VPSLKYSLLF LPTPKGASLM DIYLDRLATP | 303 |
| Consensus | QLLHFLLDRD FLSPQTTDYQ VPSLKYSLLF LPTPKGASLM DIYLDRLATP | 550 |
| | | |
| pj01304GS | WGLADNYTSV TGMDLGLKQE LLRHFLVQDT VYPLLALVAI FFGMALYLRS | 600 |
| pj01304s1 | WGLADNYTSV TGMDLGLKQE LLRHFLVQDT VYPLLALVAI FFGMALYLRS | 353 |
| Consensus | WGLADNYTSV TGMDLGLKQE LLRHFLVQDT VYPLLALVAI FFGMALYLRS | 600 |
| | | |
| pj01304GS | LFLTLMVLLG VLGSLLVAFF LYQVAFRMAY FPFVNLAALL LLSSVCANHT | 650 |
| pj01304s1 | LFLTLMVLLG VLGSLLVAFF LYQVAFRMAY FPFVNLAALL LLSSVCANHT | 403 |
| Consensus | LFLTLMVLLG VLGSLLVAFF LYQVAFRMAY FRFVNLAALL LLSSVCANHT | 650 |
| | | |
| pj01304GS | LIFFDLWRLS KSQLPSGGLA QRVGRTMHHF GYLLLVSGLT TSAAFYASYL | 700 |
| pj01304s1 | LIFFDLWRLS KSQLPSGGLA QRVGRTMHHF GYLLLVSGLT TSAAFYASYL | 453 |
| Consensus | LIFFDLWRLS KSQLPSGGLA QRVGRTMHHF GYLLLVSGLT TSAAFYASYL | 700 |
| | | |
| pj01304GS | SRLPAVRCLA LFMGTAVLVH LALTLVWLPA SAVLHERYLA RGCARRARGR | 750 |
| pj01304s1 | SRLPAVRCLA LFMGTAVLVH LALTLVWLPA SAVLHERYLA RGCARRARGR | 503 |
| Consensus | SRLPAVRCLA LFMGTAVLVH LALTLVWLPA SAVLHERYLA RGCARRARGR | 750 |
| | | |
| pj01304GS | WEGSAPRRLL LALHRRLRGL RRAAAGTSRL LFQRLLPCGV IKFRYIWICW | 800 |
| pj01304s1 | WEGSAPRRLL LALHRRLRGL RRAAAGTSRL LFQRLLPCGV IKFRYIWICW | 553 |
| Consensus | WEGSAPRRLL LALHRRLRGL RRAAAGTSRL LFQRLLPCGV IKFRYIWICW | 800 |
| | | |
| pj01304GS | FAALAAGGAY IAGVSPRLRL PTLPPGGQV FRPSHPFERF DAEYRQLFLF | 850 |
| pj01304s1 | FAALAAGGAY IAGVSPRLRL PTLPPGGQV FRPSHPFERF DAEYRQLFLF | 603 |
| Consensus | FAALAAGGAY IAGVSPRLRL PTLPPGGQV FRPSHPPERF DAEYRQLFLF | 850 |
| | | |
| pj01304GS | EQLPQGEGGH MPVVLVWGVL PVDTGDPLDP RSNSSLVRDP AFSASGPEAQ | 900 |
| pj01304s1 | EQLPQGEGGH MPVVLVWGVL PVDTGDPLDP RSNSSLVRDP AFSASGPEAQ | 653 |
| Consensus | EQLPQGEGGH MPVVLVWGVL PVDTGDPLDP RSNSSLVRDP AFSASGPEAQ | 900 |
| | | |
| pj01304GS | RWLLALCHRA RNQSFFDTLQ EGWPRLCFVE TLQRWMESPS CARLGPDLCC | 950 |
| pj01304s1 | RWLLALCHRA RNQSFFDTLQ EGWPTLCFVE TLQRWMESPS CARLGPDLCC | 703 |
| Consensus | RWLLALCHRA RNQSFFDTLQ EGWPTLCFVE TLQRWMESPS CARLGPDLCC | 950 |
| | | |
| pj01304GS | GHSDFPWAPQ FFLHCLKMMA LEQGPDGTQD LGLTFDAHGS LAALVLQFQT | 1000 |
| pj01304s1 | GHSDFPWAPQ FFLHCLKMMA LEQGPDGTQD LGLRFDAHGS LAALVLQFQT | 753 |
| Consensus | GHSDFPWAPQ FFLHCLKMMA LEQGPDGTQD LGLRFDAHGS LAALVLQFQT | 1000 |
| | | |
| pj01304GS | NFRNSPDYNQ TQLFYNEVSH WLAAELGMAP PGLRRGWFTS RLELYSLQHS | 1050 |
| pj01304s1 | NFRNSPDYNQ TQLFYNEVSH WLAAELGMAP PGLRRGWFTS RLELYSLQHS | 803 |
| Consensus | NFRNSPDYNQ TQLFYNEVSH WLAAELGMAP PGLRRGWFTS RLELYSLQHS | 1050 |
| | | |
| pj01304GS | LSTEPAVVLG LALALAFATL LLGTWNVPLS LFSVAAVAGT VLLTVGLLVL | 1100 |
| pj01304s1 | LSTEPAVVLG LALALAFATL LLGTWNVPLS LFSVAAVAGT VLLTVGLLVL | 853 |
| Consensus | LSTEPAVVLG LALALAFATL LLGTWNVPLS LFSVAAVAGT VLLTVGLLVL | 1100 |

TABLE 4-continued

| | | |
|---|---|---|
| pj01304GS | LEWQLNTAEA LFLSASVGLS VDFTVNYCIS YHLCPHPDRL SRVAFSLRQT | 1150 |
| pj01304s1 | LEWQLNTAEA LFLSASVGLS VDFTVNYCIS YHLCPHPDRL SRVAFSLRQT | 903 |
| Consensus | LEWQLNTAEA LFLSASVGLS VDFTVNYCIS YHLCPHPDRL SRVAFSLRQT | 1150 |
| pj01304GS | SCATAVGAAA LFAAGVLMLP ATVLLYRKLG IILMMVKCVS CGFASFFFQS | 1200 |
| pj01304s1 | SCATAVGAAA LFAAGVLMLP ATVLLYRKLG IILMMVKCVS CGFASFFFQS | 953 |
| Consensus | SCATAVGAAA LFAAGVLMLP ATVLLYRKLG IILMMVKCVS CGFASFFFQS | 1200 |
| pj01304GS | LCCFFGPEKN CGQILWPCAH LPWDAGTGDP GGEKAGRPRP GSVGGMPGSC | 1250 |
| pj01304s1 | LCCFFGPEKN CGQILWPCAH LPWDAGTGDP GGEKAGRPRP GSVGGMPGSC | 1003 |
| Consensus | LCCFFGPEKN CGQILWPCAH LPWDAGTGDP GGEKAGRPRP GSVGGMPGSC | 1250 |
| pj01304GS | SEQYELQPLA RRRSPSFDTS TATSKLSHRP SVLSEDLQLH DGPCCSRPPP | 1300 |
| pj01304s1 | SEQYELQPLA RRRSPSFDTS TATSKLSHRP SVLSEDLQLH DGPCCSRPPP | 1053 |
| Consensus | SEQYELQPLA RRRSPSFDTS TATSKLSHRP SVLSEDLQLH DGPCCSRPPP | 1300 |
| pj01304GS | APASPRELLL DHQAVFSQCP ALQTSSPYKQ AGPSPKTRAR QDSQGEEAEP | 1350 |
| pj01304s1 | APASPRELLL DHQAVFSQCP ALQTSSPYKQ AGPSPKTRAR QDSQGEEAEP | 1103 |
| Consensus | APASPRELLL DHQAVFSQCP ALQTSSPYKQ AGPSPKTRAR QDSQGEEAEP | 1350 |
| pj01304GS | LPASPEAPAH SPKAKAADPP DGFCSSASTL EGLSVSDETC LSTSEPSARV | 1400 |
| pj01304s1 | LPASPEAPAH SPKAKAADPP DGFCSSASTL EGLSVSDETC LSTSEPSARV | 1153 |
| Consensus | LPASPEAPAH SPKAKAADPP DGFCSSASTL EGLSVSDETC LSTSEPSARV | 1400 |
| pj01304GS | PDSVGVSPDD LDDTGQPVLE RGQLNGKRDT LWLALRETVY DPSLPASHHS | 1450 |
| pj01304s1 | PDSVGVSPDD LDDTGQPVLE RGQLNGKRDT LWLALRETVY DPSLPASHHS | 1203 |
| Consensus | PDSVGVSPDD LDDTGQPVLE RGQLNGKRDT LWLALRETVY DPSLPASHHS | 1450 |
| pj01304GS | SLSWKGRGGP GDGSPVVLPN SQPDLPDVWL RRPSTHTSGY SS | 1492 |
| pj01304s1 | SLSWKGRGGP GDGSPVVLPN SQPDLPDVWL RRPSTHTSGY SS | 1245 |
| Consensus | SLSWKGRGGP GDGSPVVLPN SQPDLPDVWL RRPSTHTSGY SS | 1492 |

INDUSTRIAL APPLICABILITY

In view of the above knowledge and information, it is considered that the present DNA is a cancer-associated gene, and that it is possible to inhibit cancer by blocking the binding of the present protein to its ligand.

Accordingly, the present antibody is used not only in the detection of the present protein, but also as an agent for the treatment or prevention of cancers such as prostatic adenocarcinoma and ovarian carcinoma

The invention claimed is:

1. An isolated DNA consisting of the nucleotide sequence encoding
   the polypeptide consisting of the amino acid sequence of SEQ ID NO: 18.

2. An isolated DNA consisting of the nucleotide sequence of SEQ ID NO:1 or the nucleotide sequence consisting of nucleotides 561-4295 of SEQ ID NO: 1.

3. An isolated gene comprising the DNA of claim 1 or claim 2.

4. An expression vector comprising the isolated DNA of claim 1 or 2 or an isolated gene comprising the DNA of claim 1 or claim 2.

5. A isolated transformant transformed with the expression vector of claim 4.

6. A method for the expression of an isolated DNA comprising culturing the transformant of claim 5.

7. A method for the production of a protein, comprising:
   culturing the transformant of claim 5, and
   recovering the protein expressed from said transformant or the culture supernatant thereof, wherein the protein is encoded by the nucleotide consisting of nucleotides 561-4295 of SEQ ID NO: 1.

* * * * *

SEQUENCE LISTING

```
<160> NUMBER OF SEQ ID NOS: 5

<210> SEQ ID NO 1
<211> LENGTH: 5035
<212> TYPE: DNA
<213> ORGANISM: Homo sapiens
<220> FEATURE:
<221> NAME/KEY: CDS
<222> LOCATION: (561)..(4295)

<400> SEQUENCE: 1
ctcgccgccg ctgccgccgc caccgccgcc gccgccgccg ccgccgccgc ggcttcagca        60
ccagcgcccg gacagcggtg ccgcccacgg gcatggacgg tgacagcagc agcagcagcg       120
gcggcagcgg tccggctccc ggcccgggtc cggaagggga gcaacggccc gagggggagc       180
ccttggcccc agacggcggc tccccggaca gcacccagac caaggctgtg gcccctgagg       240
caagcccaga gagaagctcc tccctccaca gctgcccct ggaggaccct ttcagctctt       300 taggacccc accaacaact ttcaccctcc agcctgtggg tccatccagc ccttggccc       360 ctgcccactt tacctatacc cgggcactgt aggaatacca gggggcagt tccctgccag       420
```

```
gacttgggga tcgggcagct ctctgctccc acggctccag cctcagccct tctccagccc    480
cctcacagcg cgatgggacc tggaagccac ccgctgtgca gcaccatgtg gtcagcgtca    540
ggcaggaacg agccttccag atg cca aag agc tat tcc cag ctg att gct gag   593
                      Met Pro Lys Ser Tyr Ser Gln Leu Ile Ala Glu
                       1               5                   10 tgg cca gtg gcc gtg ctg atg ctg tgt ctg gct gtc atc ttc ctc tgc     641
Trp Pro Val Ala Val Leu Met Leu Cys Leu Ala Val Ile Phe Leu Cys
            15                  20                  25 acc ctg gct gga ctg ttg ggg gcc cgg ctg ccc gac ttc tcc aag cct     689
Thr Leu Ala Gly Leu Leu Gly Ala Arg Leu Pro Asp Phe Ser Lys Pro
        30                  35                  40 ttg ctg ggc ttt gag cca cgg gac aca gac att ggg agc aag tta gtg     737
Leu Leu Gly Phe Glu Pro Arg Asp Thr Asp Ile Gly Ser Lys Leu Val
    45                  50                  55 gtc tgg aga gca cta caa gcc ctc aca ggc ccc agg aag ctg ctt ttc     785
Val Trp Arg Ala Leu Gln Ala Leu Thr Gly Pro Arg Lys Leu Leu Phe
60                  65                  70                  75 ctt tcc cca gac ctt gag ctg aac agc tcg agc tcc cac aac act ctg     833
Leu Ser Pro Asp Leu Glu Leu Asn Ser Ser Ser His Asn Thr Leu
                80                  85                  90 agg cct gca ccc aga ggc agt gcc cag gag agc gct gtc cgg cct cgg     881
Arg Pro Ala Pro Arg Gly Ser Ala Gln Glu Ser Ala Val Arg Pro Arg
            95                  100                 105 aga atg gtg gag ccc ctg gag gac aga agg caa gag aac ttc ttc tgt     929
Arg Met Val Glu Pro Leu Glu Asp Arg Arg Gln Glu Asn Phe Phe Cys
        110                 115                 120 ggc ccc cct gag aag agc tat gca aag ctg gtg ttc atg tcc acc tcc     977
Gly Pro Pro Glu Lys Ser Tyr Ala Lys Leu Val Phe Met Ser Thr Ser
    125                 130                 135 tcg ggc agc cta tgg aac ctg cat gcc atc cat tcc atg tgt cgc atg    1025
Ser Gly Ser Leu Trp Asn Leu His Ala Ile His Ser Met Cys Arg Met
140                 145                 150                 155 gaa cag gac cag atc cgc tcc cat acc agc ttc ggg gct ctg tgc cag    1073
Glu Gln Asp Gln Ile Arg Ser His Thr Ser Phe Gly Ala Leu Cys Gln
                160                 165                 170 cgg aca gca gcc aac cag tgc tgc ccc agc tgg tcc ctg ggc aac tat    1121
Arg Thr Ala Ala Asn Gln Cys Cys Pro Ser Trp Ser Leu Gly Asn Tyr
            175                 180                 185 ctg gct gtg ctc tcc aac cgc tcc tcc tgc ctg gac act acc caa gct    1169
Leu Ala Val Leu Ser Asn Arg Ser Ser Cys Leu Asp Thr Thr Gln Ala
        190                 195                 200 gac gca gcc cgc aca ctg gcc ctg ctt cgg acc tgt gcc ctc tac tac    1217
Asp Ala Ala Arg Thr Leu Ala Leu Leu Arg Thr Cys Ala Leu Tyr Tyr
205                 210                 215 cac agt ggc gcc ttg gtg ccc tct tgt ctg gga cct ggg cag aac aag    1265
His Ser Gly Ala Leu Val Pro Ser Cys Leu Gly Pro Gly Gln Asn Lys
220                 225                 230                 235 tcc cca cgc tgt gcc cag gtt ccc acc aag tgc tcc cag agt agt gcc    1313
Ser Pro Arg Cys Ala Gln Val Pro Thr Lys Cys Ser Gln Ser Ser Ala
                240                 245                 250 atc tac caa ctc ctg cac ttt ctg ctt gac agg gac ttt ctg agt ccc    1361
Ile Tyr Gln Leu Leu His Phe Leu Leu Asp Arg Asp Phe Leu Ser Pro
            255                 260                 265 cag acc act gac tac cag gtg cct tcc ctc aag tac agc ctg ctc ttc    1409
Gln Thr Thr Asp Tyr Gln Val Pro Ser Leu Lys Tyr Ser Leu Leu Phe
        270                 275                 280 ctg ccc acc cca aag ggt gct tcc ctc atg gac atc tac ctg gac cgg    1457
Leu Pro Thr Pro Lys Gly Ala Ser Leu Met Asp Ile Tyr Leu Asp Arg
285                 290                 295
```

-continued

| | |
|---|---|
| ctg gcc acc ccc tgg ggg ctt gct gac aac tac acc tct gtc act ggc<br>Leu Ala Thr Pro Trp Gly Leu Ala Asp Asn Tyr Thr Ser Val Thr Gly<br>300                   305                   310                   315 | 1505 |
| atg gac ctg ggc ctc aag cag gag ctg ctg agg cac ttc ctg gtc cag<br>Met Asp Leu Gly Leu Lys Gln Glu Leu Leu Arg His Phe Leu Val Gln<br>                320                   325                   330 | 1553 |
| gac acg gtg tac ccc ttg ctg gct ctg gtt gcc atc ttc ttc ggc atg<br>Asp Thr Val Tyr Pro Leu Leu Ala Leu Val Ala Ile Phe Phe Gly Met<br>               335                   340                   345 | 1601 |
| gcc ctg tac ctg cgc tca ctc ttc ctc acg ctc atg gtg ctg ctg ggg<br>Ala Leu Tyr Leu Arg Ser Leu Phe Leu Thr Leu Met Val Leu Leu Gly<br>350                   355                   360 | 1649 |
| gtg ctg ggc tca ctg ctg gtg gcc ttc ttc ctt tac cag gtg gcc ttc<br>Val Leu Gly Ser Leu Leu Val Ala Phe Phe Leu Tyr Gln Val Ala Phe<br>365                   370                   375 | 1697 |
| cgc atg gcc tac ttc ccc ttc gtc aat ctg gca gcc ctc ctc ctg ctg<br>Arg Met Ala Tyr Phe Pro Phe Val Asn Leu Ala Ala Leu Leu Leu Leu<br>380                   385                   390                   395 | 1745 |
| agc agc gtc tgc gcc aac cac acg ctc atc ttc ttc gac ctg tgg cgc<br>Ser Ser Val Cys Ala Asn His Thr Leu Ile Phe Phe Asp Leu Trp Arg<br>                      400                   405                   410 | 1793 |
| ctt agc aag agc cag ctg ccg tcg ggg ggg ctg gcg cag cgc gtg ggc<br>Leu Ser Lys Ser Gln Leu Pro Ser Gly Gly Leu Ala Gln Arg Val Gly<br>               415                   420                   425 | 1841 |
| cgc acc atg cac cac ttc ggc tac ctg ctg ctg gtc tcc ggc ctc acc<br>Arg Thr Met His His Phe Gly Tyr Leu Leu Leu Val Ser Gly Leu Thr<br>430                   435                   440 | 1889 |
| acg agc gcg gcc ttc tat gcc agc tac ctg agc cgc ctg ccg gcc gtt<br>Thr Ser Ala Ala Phe Tyr Ala Ser Tyr Leu Ser Arg Leu Pro Ala Val<br>445                   450                   455 | 1937 |
| cgc tgc ctc gcc ctc ttc atg ggc acg gct gtg ctg gtg cac ctg gcg<br>Arg Cys Leu Ala Leu Phe Met Gly Thr Ala Val Leu Val His Leu Ala<br>460                   465                   470                   475 | 1985 |
| ctc acg ctg gtc tgg ctg ccc gcc tcc gcc gtg ctc cac gag cgc tac<br>Leu Thr Leu Val Trp Leu Pro Ala Ser Ala Val Leu His Glu Arg Tyr<br>                      480                   485                   490 | 2033 |
| ctg gcg cgc ggc tgt gcg cgc cgg gcg cgg ggc cgg tgg gag ggc agc<br>Leu Ala Arg Gly Cys Ala Arg Arg Ala Arg Gly Arg Trp Glu Gly Ser<br>               495                   500                   505 | 2081 |
| gcg ccc cgg cgg cta ctg ctg gcg ctg cac cgg cgg ctc cgc ggc ctg<br>Ala Pro Arg Arg Leu Leu Leu Ala Leu His Arg Arg Leu Arg Gly Leu<br>510                   515                   520 | 2129 |
| cgg agg gcg gcg gct ggc acc tcg cgt ctg ctc ttc cag cgc ctg ctg<br>Arg Arg Ala Ala Ala Gly Thr Ser Arg Leu Leu Phe Gln Arg Leu Leu<br>525                   530                   535 | 2177 |
| ccc tgc ggc gtc atc aag ttc cgc tac atc tgg atc tgc tgg ttc gca<br>Pro Cys Gly Val Ile Lys Phe Arg Tyr Ile Trp Ile Cys Trp Phe Ala<br>540                   545                   550                   555 | 2225 |
| gca ctg gcg gca ggg ggc gcc tac atc gcc gga gtc agc ccc cgc ctg<br>Ala Leu Ala Ala Gly Gly Ala Tyr Ile Ala Gly Val Ser Pro Arg Leu<br>                      560                   565                   570 | 2273 |
| cgg ctg ccc acg ctg ccg ccg ccc ggc ggc cag gtc ttc cgg ccc agc<br>Arg Leu Pro Thr Leu Pro Pro Pro Gly Gly Gln Val Phe Arg Pro Ser<br>               575                   580                   585 | 2321 |
| cac ccc ttc gag cgc ttc gac gca gag tat cgc cag ctg ttc ctg ttc<br>His Pro Phe Glu Arg Phe Asp Ala Glu Tyr Arg Gln Leu Phe Leu Phe<br>590                   595                   600 | 2369 |
| gag cag ctg ccg cag ggc gag ggc ggc cac atg ccc gtg gtt ttg gtg<br>Glu Gln Leu Pro Gln Gly Glu Gly Gly His Met Pro Val Val Leu Val<br>605                   610                   615 | 2417 |

```
tgg ggc gtc ctg cct gtg gac act ggc gac cct ctg gac cct cgt agc    2465
Trp Gly Val Leu Pro Val Asp Thr Gly Asp Pro Leu Asp Pro Arg Ser
620                 625                 630                 635 aac agc agc ctg gtg agg gac cct gcc ttc tcg gcc agc ggc cct gag    2513
Asn Ser Ser Leu Val Arg Asp Pro Ala Phe Ser Ala Ser Gly Pro Glu
                640                 645                 650 gcc cag cgc tgg ctg ctg gca ctc tgt cac cgg gcc cgg aat cag agc    2561
Ala Gln Arg Trp Leu Leu Ala Leu Cys His Arg Ala Arg Asn Gln Ser
        655                 660                 665 ttc ttc gac acc ctg cag gaa ggc tgg ccc acg ctg tgt ttc gtg gag    2609
Phe Phe Asp Thr Leu Gln Glu Gly Trp Pro Thr Leu Cys Phe Val Glu
                670                 675                 680 acc ctc cag cgc tgg atg gag agc ccc agc tgc gcc cgc ctg ggg cct    2657
Thr Leu Gln Arg Trp Met Glu Ser Pro Ser Cys Ala Arg Leu Gly Pro
685                 690                 695 gac ctc tgc tgc ggc cac tcg gac ttc ccc tgg gcc ccc cag ttt ttc    2705
Asp Leu Cys Cys Gly His Ser Asp Phe Pro Trp Ala Pro Gln Phe Phe
700                 705                 710                 715 ctg cac tgc ctg aaa atg atg gct ctg gag caa ggc ccc gat ggc acc    2753
Leu His Cys Leu Lys Met Met Ala Leu Glu Gln Gly Pro Asp Gly Thr
                720                 725                 730 cag gac ctg gga ctc cgc ttt gat gcc cat ggc agc ctg gcc gcc ctg    2801
Gln Asp Leu Gly Leu Arg Phe Asp Ala His Gly Ser Leu Ala Ala Leu
        735                 740                 745 gtc cta caa ttc cag acc aac ttc cgg aac agt ccg gac tac aac cag    2849
Val Leu Gln Phe Gln Thr Asn Phe Arg Asn Ser Pro Asp Tyr Asn Gln
        750                 755                 760 acc cag ctc ttc tac aat gag gtc agc cac tgg ctg gca gcg gag ctg    2897
Thr Gln Leu Phe Tyr Asn Glu Val Ser His Trp Leu Ala Ala Glu Leu
765                 770                 775 ggc atg gca cct cca ggc ctc cgc cgt ggt tgg ttc act agc cgt cta    2945
Gly Met Ala Pro Pro Gly Leu Arg Arg Gly Trp Phe Thr Ser Arg Leu
780                 785                 790                 795 gag ctg tat agc ctg cag cac agc ctg agc act gag cct gct gtg gtg    2993
Glu Leu Tyr Ser Leu Gln His Ser Leu Ser Thr Glu Pro Ala Val Val
                800                 805                 810 ctg ggc ctg gct ttg gcg ctg gcc ttt gcc aca ctg ctc ctg ggc acc    3041
Leu Gly Leu Ala Leu Ala Leu Ala Phe Ala Thr Leu Leu Leu Gly Thr
        815                 820                 825 tgg aat gtt ccc ctc agc cta ttc tcc gtg gca gct gtg gca ggc acc    3089
Trp Asn Val Pro Leu Ser Leu Phe Ser Val Ala Ala Val Ala Gly Thr
        830                 835                 840 gtg ctg ctc act gta gga ctc ctg gtt ctc gag tgg cag ctc aac        3137
Val Leu Leu Thr Val Gly Leu Leu Val Leu Glu Trp Gln Leu Asn
845                 850                 855 act gcc gag gcc ctg ttt ctc tct gcc tca gtg ggc ctc tca gta gac    3185
Thr Ala Glu Ala Leu Phe Leu Ser Ala Ser Val Gly Leu Ser Val Asp
860                 865                 870                 875 ttc act gtc aac tac tgc atc tcc tat cac ctg tgc cca cac cct gac    3233
Phe Thr Val Asn Tyr Cys Ile Ser Tyr His Leu Cys Pro His Pro Asp
                880                 885                 890 cgc ctg agc cgt gtg gcc ttc tct ctg cgc cag acc agc tgc gcc aca    3281
Arg Leu Ser Arg Val Ala Phe Ser Leu Arg Gln Thr Ser Cys Ala Thr
        895                 900                 905 gcc gtg ggg gct gca gcc ctg ttt gcg gca ggc gtg ctc atg ctg cct    3329
Ala Val Gly Ala Ala Ala Leu Phe Ala Ala Gly Val Leu Met Leu Pro
            910                 915                 920 gcc aca gtg ctg ctc tat cgc aag ctg ggc atc atc ctc atg atg gtc    3377
Ala Thr Val Leu Leu Tyr Arg Lys Leu Gly Ile Ile Leu Met Met Val
925                 930                 935
```

-continued

```
aaa tgc gtc agt tgt ggc ttt gcc agc ttc ttc ttc caa tct ctc tgc     3425
Lys Cys Val Ser Cys Gly Phe Ala Ser Phe Phe Phe Gln Ser Leu Cys
940             945                 950                 955 tgt ttc ttc ggg cca gag aag aac tgt ggg cag atc ctc tgg ccc tgt     3473
Cys Phe Phe Gly Pro Glu Lys Asn Cys Gly Gln Ile Leu Trp Pro Cys
            960                 965                 970 gcc cac ctg cca tgg gat gct ggt act ggg gac cct ggt ggg gag aag     3521
Ala His Leu Pro Trp Asp Ala Gly Thr Gly Asp Pro Gly Gly Glu Lys
    975                 980                 985 gca ggc cgc cca cga cca ggg tca gtg gga ggg atg ccc ggg tcc tgc     3569
Ala Gly Arg Pro Arg Pro Gly Ser Val Gly Gly Met Pro Gly Ser Cys
990                 995                 1000 tca gag caa tat gag cta cag ccc ctg gca cgg cgt cgg agc ccc agc     3617
Ser Glu Gln Tyr Glu Leu Gln Pro Leu Ala Arg Arg Arg Ser Pro Ser
        1005                1010                1015 ttt gac acc agc aca gcc acc agc aag ctg tcc cac cgg ccc tca gta     3665
Phe Asp Thr Ser Thr Ala Thr Ser Lys Leu Ser His Arg Pro Ser Val
1020                1025                1030                1035 ctc tct gag gat ctg cag ctc cat gat ggt ccg tgc tgt tcc cgg ccc     3713
Leu Ser Glu Asp Leu Gln Leu His Asp Gly Pro Cys Cys Ser Arg Pro
            1040                1045                1050 cca cca gcc cct gcc tcc cca agg gag ctg ctg ctg gac cac cag gca     3761
Pro Pro Ala Pro Ala Ser Pro Arg Glu Leu Leu Leu Asp His Gln Ala
    1055                1060                1065 gtc ttc agc cag tgc cct gcc ctg cag acc tcc tcc cct tat aag cag     3809
Val Phe Ser Gln Cys Pro Ala Leu Gln Thr Ser Ser Pro Tyr Lys Gln
1070                1075                1080 gct ggc ccc agc ccc aaa acc cgg gcc agg cag gac tcc caa ggg gag     3857
Ala Gly Pro Ser Pro Lys Thr Arg Ala Arg Gln Asp Ser Gln Gly Glu
        1085                1090                1095 gag gct gag ccc ctg cca gcc tca cca gaa gcc cca gcc cac tct cct     3905
Glu Ala Glu Pro Leu Pro Ala Ser Pro Glu Ala Pro Ala His Ser Pro
1100                1105                1110                1115 aag gcc aag gct gca gat cct cct gat ggc ttc tgt tcc tca gcc agc     3953
Lys Ala Lys Ala Ala Asp Pro Pro Asp Gly Phe Cys Ser Ser Ala Ser
            1120                1125                1130 acc ctg gag ggg ctc agc gtc tct gat gag acc tgc cta agc acc tct     4001
Thr Leu Glu Gly Leu Ser Val Ser Asp Glu Thr Cys Leu Ser Thr Ser
    1135                1140                1145 gag ccc agt gcc cgt gta cca gat tcc gtg ggt gtg tcc cca gat gac     4049
Glu Pro Ser Ala Arg Val Pro Asp Ser Val Gly Val Ser Pro Asp Asp
1150                1155                1160 ctg gat gac act ggg cag cca gtc ctt gag cga ggc cag ctc aat ggg     4097
Leu Asp Asp Thr Gly Gln Pro Val Leu Glu Arg Gly Gln Leu Asn Gly
        1165                1170                1175 aag cgg gac acc ctg tgg ctg gcg ctg agg gag aca gtg tat gac cca     4145
Lys Arg Asp Thr Leu Trp Leu Ala Leu Arg Glu Thr Val Tyr Asp Pro
1180                1185                1190                1195 tca ttg ccc gct tcc cat cac agc agc ttg tcc tgg aag ggc cga ggg     4193
Ser Leu Pro Ala Ser His His Ser Ser Leu Ser Trp Lys Gly Arg Gly
            1200                1205                1210 ggg cca ggg gat ggc agc cct gtg gtg ctg ccc aat agc cag cca gac     4241
Gly Pro Gly Asp Gly Ser Pro Val Val Leu Pro Asn Ser Gln Pro Asp
    1215                1220                1225 ctg cca gat gtt tgg ctg cgc agg ccc agc act cac acg tca ggc tat     4289
Leu Pro Asp Val Trp Leu Arg Arg Pro Ser Thr His Thr Ser Gly Tyr
1230                1235                1240 agc agc tgagggggac ccggggaggc tggacagggc gcggaaccct gtcatggatg      4345
Ser Ser
    1245
```

-continued

```
acaaggcaag ggcagcaata ggctggagcc cgaaggtatt tctccagatc cacagggaga    4405
ggtctcaccc tccagctgtg gatgttaaac cctgccagat gtcccagcct tgatctgtct    4465
gctcctactc ctcacatctg gaggattcca gcaggagggg ttttggaggg gacctgcttg    4525
cgacctgctg agggcttgtc tgctcccaca gcaccatcta agaccectcc tctagaagtg    4585 gggaaggcca gatgtgtagc ttcgggtatc agaggaggct gacctggccc ccatcccaag    4645
ttacaagaac ttcagtgaga ctaagggacc cccatcctag ggatcttgtc agggttcctt    4705
actgaccaga ggagcccgca gcaatctcca cagcctcctg ggtctcaccc ctttcatggg    4765
ctcttcatca ggacacttcc ctctcttttg ggagcttctc tgggcagaat tgggctggga    4825
cctctctccc caactgccct gctctcctca tactcaccgg tttgaccaga aattctccaa    4885
atccagccat agatggctgc tgggtgtgca gcaggagaag gaggatggtc agccttggag    4945
catctctcaa ttacgggaca gtccctcttt ggaagcaggc tcctgtgctt tcctgtgtta    5005
ataaacagta ataatccttt ccatctctgc                                     5035
```

<210> SEQ ID NO 2
<211> LENGTH: 4479
<212> TYPE: DNA
<213> ORGANISM: Homo sapiens
<220> FEATURE:
<221> NAME/KEY: CDS
<222> LOCATION: (1)..(4476)

<400> SEQUENCE: 2

```
atg gga aga aag acc caa cct gat gcc tcg ccc cac tgg gga ggg gag         48
Met Gly Arg Lys Thr Gln Pro Asp Ala Ser Pro His Trp Gly Gly Glu
 1               5                  10                  15 gag ggc gct gag cga gcc ggg aac ctc gca ggc ctg aag ccg ccc gcc         96
Glu Gly Ala Glu Arg Ala Gly Asn Leu Ala Gly Leu Lys Pro Pro Ala
             20                  25                  30 tcg acc cgg ggc gtc cag cgt ggt gaa gtg cgg gcg tgg agc tcg ccc        144
Ser Thr Arg Gly Val Gln Arg Gly Glu Val Arg Ala Trp Ser Ser Pro
         35                  40                  45 tct atc cgg ctg gaa gga gcc tac gca tgc gca cga gca ccc cgc cgc        192
Ser Ile Arg Leu Glu Gly Ala Tyr Ala Cys Ala Arg Ala Pro Arg Arg
     50                  55                  60 cgc tgc cgc cgc cac cgc cgc cgc cgc cgc cgc cgc cgc ggc ttc agc        240
Arg Cys Arg Arg His Arg Arg Arg Arg Arg Arg Arg Arg Gly Phe Ser
 65                  70                  75                  80 acc agc gcc cgg aca gcg gtg ccg ccc acg ggc atg gac ggt gac agc        288
Thr Ser Ala Arg Thr Ala Val Pro Pro Thr Gly Met Asp Gly Asp Ser
                 85                  90                  95 agc agc agc agc ggc ggc agc ggt ccg gct ccc ggc ccg ggt ccg gaa        336
Ser Ser Ser Ser Gly Gly Ser Gly Pro Ala Pro Gly Pro Gly Pro Glu
            100                 105                 110 ggg gag caa cgg ccc gag ggg gag ccc ttg gcc cca gac ggc ggc tcc        384
Gly Glu Gln Arg Pro Glu Gly Glu Pro Leu Ala Pro Asp Gly Gly Ser
        115                 120                 125 ccg gac agc acc cag acc aag gct gtg ccc cct gag gca agc cca gag        432
Pro Asp Ser Thr Gln Thr Lys Ala Val Pro Pro Glu Ala Ser Pro Glu
    130                 135                 140 aga agc tgc tcc ctc cac agc tgc ccc ctg gag gac cct tcc agc tct        480
Arg Ser Cys Ser Leu His Ser Cys Pro Leu Glu Asp Pro Ser Ser Ser
145                 150                 155                 160 tca gga ccc cca cca aca act tcc acc ctc cag cct gtg ggt cca tcc        528
Ser Gly Pro Pro Pro Thr Thr Ser Thr Leu Gln Pro Val Gly Pro Ser
                165                 170                 175
```

-continued

| | |
|---|---|
| agc ccc ttg gcc cct gcc cac ttc acc tat ccc cgg gca ctg cag gaa<br>Ser Pro Leu Ala Pro Ala His Phe Thr Tyr Pro Arg Ala Leu Gln Glu<br>            180                    185                   190 | 576 |
| tac cag ggg ggc agt tcc ctg cca gga ctt ggg gat cgg gca gct ctc<br>Tyr Gln Gly Gly Ser Ser Leu Pro Gly Leu Gly Asp Arg Ala Ala Leu<br>            195                    200                   205 | 624 |
| tgc tcc cac ggc tcc agc ctc agc cct tct cca gcc ccc tca cag cgc<br>Cys Ser His Gly Ser Ser Leu Ser Pro Ser Pro Ala Pro Ser Gln Arg<br>        210                    215                   220 | 672 |
| gat ggg acc tgg aag cca ccc gct gtg cag cac cat gtg gtc agc gtc<br>Asp Gly Thr Trp Lys Pro Pro Ala Val Gln His His Val Val Ser Val<br>225                   230                   235                   240 | 720 |
| agg cag gaa cga gcc ttc cag atg cca aag agc tat tcc cag ctg att<br>Arg Gln Glu Arg Ala Phe Gln Met Pro Lys Ser Tyr Ser Gln Leu Ile<br>                  245                    250                   255 | 768 |
| gct gag tgg cca gtg gcc gtg ctg atg ctg tgt ctg gct gtc atc ttc<br>Ala Glu Trp Pro Val Ala Val Leu Met Leu Cys Leu Ala Val Ile Phe<br>            260                    265                   270 | 816 |
| ctc tgc acc ctg gct gga ctt ggg gcc cgg ctg ccc gac ttc tcc<br>Leu Cys Thr Leu Ala Gly Leu Leu Gly Ala Arg Leu Pro Asp Phe Ser<br>        275                    280                   285 | 864 |
| aag cct ttg ctg ggc ttt gag cca cgg gac aca gac att ggg agc aag<br>Lys Pro Leu Leu Gly Phe Glu Pro Arg Asp Thr Asp Ile Gly Ser Lys<br>            290                    295                   300 | 912 |
| tta gtg gtc tgg aga gca cta caa gcc ctc aca ggc ccc agg aag ctg<br>Leu Val Val Trp Arg Ala Leu Gln Ala Leu Thr Gly Pro Arg Lys Leu<br>305                   310                   315                   320 | 960 |
| ctt ttc ctt tcc cca gac ctt gag ctg aac agc tcg agc tcc cac aac<br>Leu Phe Leu Ser Pro Asp Leu Glu Leu Asn Ser Ser Ser Ser His Asn<br>                  325                    330                   335 | 1008 |
| act ctg agg cct gca ccc aga ggc agt gcc cag gag agc gct gtc cgg<br>Thr Leu Arg Pro Ala Pro Arg Gly Ser Ala Gln Glu Ser Ala Val Arg<br>            340                    345                   350 | 1056 |
| cct cgg aga atg gtg gag ccc ctg gag gac aga agg caa gag aac ttc<br>Pro Arg Arg Met Val Glu Pro Leu Glu Asp Arg Arg Gln Glu Asn Phe<br>                  355                    360                   365 | 1104 |
| ttc tgt ggc ccc cct gag aag agc tat gca aag ctg gtg ttc atg tcc<br>Phe Cys Gly Pro Pro Glu Lys Ser Tyr Ala Lys Leu Val Phe Met Ser<br>        370                    375                   380 | 1152 |
| acc tcc tcg ggc agc cta tgg aac ctg cat gcc atc cat tcc atg tgt<br>Thr Ser Ser Gly Ser Leu Trp Asn Leu His Ala Ile His Ser Met Cys<br>385                   390                   395                   400 | 1200 |
| cgc atg gaa cag gac cag atc cgc tcc cat acc agc ttc ggg gct ctg<br>Arg Met Glu Gln Asp Gln Ile Arg Ser His Thr Ser Phe Gly Ala Leu<br>                  405                    410                   415 | 1248 |
| tgc cag cgg aca gca gcc aac cag tgc tgc ccc agc tgg tcc ctg ggc<br>Cys Gln Arg Thr Ala Ala Asn Gln Cys Cys Pro Ser Trp Ser Leu Gly<br>            420                    425                   430 | 1296 |
| aac tat ctg gct gtg ctc tcc aac cgc tcc tcc tgc ctg gac act acc<br>Asn Tyr Leu Ala Val Leu Ser Asn Arg Ser Ser Cys Leu Asp Thr Thr<br>                  435                    440                   445 | 1344 |
| caa gct gac gca gcc cgc aca ctg gcc ctg ctt cgg acc tgt gcc ctc<br>Gln Ala Asp Ala Ala Arg Thr Leu Ala Leu Leu Arg Thr Cys Ala Leu<br>        450                    455                   460 | 1392 |
| tac tac cac agt ggc gcc ttg gtg ccc tct tgt ctg gga cct ggg cag<br>Tyr Tyr His Ser Gly Ala Leu Val Pro Ser Cys Leu Gly Pro Gly Gln<br>465                   470                   475                   480 | 1440 |
| aac aag tcc cca cgc tgt gcc cag gtt ccc acc aag tgc tcc cag agt<br>Asn Lys Ser Pro Arg Cys Ala Gln Val Pro Thr Lys Cys Ser Gln Ser<br>                  485                    490                   495 | 1488 |

-continued

```
agt gcc atc tac caa ctc ctg cac ttt ctg ctt gac agg gac ttt ctg      1536
Ser Ala Ile Tyr Gln Leu Leu His Phe Leu Leu Asp Arg Asp Phe Leu
            500                 505                 510 agt ccc cag acc act gac tac cag gtg cct tcc ctc aag tac agc ctg      1584
Ser Pro Gln Thr Thr Asp Tyr Gln Val Pro Ser Leu Lys Tyr Ser Leu
            515                 520                 525 ctc ttc ctg ccc acc cca aag ggt gct tcc ctc atg gac atc tac ctg      1632
Leu Phe Leu Pro Thr Pro Lys Gly Ala Ser Leu Met Asp Ile Tyr Leu
    530                 535                 540 gac cgg ctg gcc acc ccc tgg ggg ctt gct gac aac tac acc tct gtc      1680
Asp Arg Leu Ala Thr Pro Trp Gly Leu Ala Asp Asn Tyr Thr Ser Val
545                 550                 555                 560 act ggc atg gac ctg ggc ctc aag cag gag ctg ctg agg cac ttc ctg      1728
Thr Gly Met Asp Leu Gly Leu Lys Gln Glu Leu Leu Arg His Phe Leu
                565                 570                 575 gtc cag gac acg gtg tac ccc ttg ctg gct ctg gtt gcc atc ttc ttc      1776
Val Gln Asp Thr Val Tyr Pro Leu Leu Ala Leu Val Ala Ile Phe Phe
            580                 585                 590 ggc atg gcc ctg tac ctg cgc tca ctc ttc ctc acg ctc atg gtg ctg      1824
Gly Met Ala Leu Tyr Leu Arg Ser Leu Phe Leu Thr Leu Met Val Leu
            595                 600                 605 ctg ggg gtg ctg ggc tca ctg ctg gtg gcc ttc ttc ctt tac cag gtg      1872
Leu Gly Val Leu Gly Ser Leu Leu Val Ala Phe Phe Leu Tyr Gln Val
    610                 615                 620 gcc ttc cgc atg gcc tac ttc ccc ttc gtc aat ctg gca gcc ctc ctc      1920
Ala Phe Arg Met Ala Tyr Phe Pro Phe Val Asn Leu Ala Ala Leu Leu
625                 630                 635                 640 ctg ctg agc agc gtc tgc gcc aac cac acg ctc atc ttc ttc gac ctg      1968
Leu Leu Ser Ser Val Cys Ala Asn His Thr Leu Ile Phe Phe Asp Leu
                645                 650                 655 tgg cgc ctt agc aag agc cag ctg ccg tcg ggg ggg ctg gcg cag cgc      2016
Trp Arg Leu Ser Lys Ser Gln Leu Pro Ser Gly Gly Leu Ala Gln Arg
            660                 665                 670 gtg ggc cgc acc atg cac cac ttc ggc tac ctg ctg ctg gtc tcc ggc      2064
Val Gly Arg Thr Met His His Phe Gly Tyr Leu Leu Leu Val Ser Gly
            675                 680                 685 ctc acc acg agc gcg gcc ttc tat gcc agc tac ctg agc cgc ctg ccg      2112
Leu Thr Thr Ser Ala Ala Phe Tyr Ala Ser Tyr Leu Ser Arg Leu Pro
    690                 695                 700 gcc gtt cgc tgc ctc gcc ctc ttc atg ggc acg gct gtg ctg gtg cac      2160
Ala Val Arg Cys Leu Ala Leu Phe Met Gly Thr Ala Val Leu Val His
705                 710                 715                 720 ctg gcg ctc acg ctg gtc tgg ctg ccc gcc tcc gcc gtg ctc cac gag      2208
Leu Ala Leu Thr Leu Val Trp Leu Pro Ala Ser Ala Val Leu His Glu
                725                 730                 735 cgc tac ctg gcg cgc ggc tgt gcg cgc cgg gcg cgg ggc cgg tgg gag      2256
Arg Tyr Leu Ala Arg Gly Cys Ala Arg Arg Ala Arg Gly Arg Trp Glu
            740                 745                 750 ggc agc gcg ccc cgg cgg cta ctg ctg gcg ctg cac cgg cgg ctc cgc      2304
Gly Ser Ala Pro Arg Arg Leu Leu Leu Ala Leu His Arg Arg Leu Arg
            755                 760                 765 ggc ctg cgg agg gcg gcg gct ggc acc tcg cgt ctg ctc ttc cag cgc      2352
Gly Leu Arg Arg Ala Ala Ala Gly Thr Ser Arg Leu Leu Phe Gln Arg
    770                 775                 780 ctg ctg ccc tgc ggc gtc atc aag ttc cgc tac atc tgg atc tgc tgg      2400
Leu Leu Pro Cys Gly Val Ile Lys Phe Arg Tyr Ile Trp Ile Cys Trp
785                 790                 795                 800 ttc gca gca ctg gcg gca ggg ggc gcc tac atc gcc gga gtc agc ccc      2448
Phe Ala Ala Leu Ala Ala Gly Gly Ala Tyr Ile Ala Gly Val Ser Pro
                805                 810                 815
```

```
                                                -continued cgc ctg cgg ctg ccc acg ctg ccg ccg ccc ggc ggc cag gtc ttc cgg    2496
Arg Leu Arg Leu Pro Thr Leu Pro Pro Pro Gly Gly Gln Val Phe Arg
            820                 825                 830 ccc agc cac ccc ttc gag cgc ttc gac gcg gag tat cgc cag ctg ttc    2544
Pro Ser His Pro Phe Glu Arg Phe Asp Ala Glu Tyr Arg Gln Leu Phe
835                 840                 845 ctg ttc gag cag ctg ccg cag ggc gag ggc ggc cac atg ccc gtg gtt    2592
Leu Phe Glu Gln Leu Pro Gln Gly Glu Gly Gly His Met Pro Val Val
    850                 855                 860 ttg gtg tgg ggc gtc ctg cct gtg gac act ggc gac cct ctg gac cct    2640
Leu Val Trp Gly Val Leu Pro Val Asp Thr Gly Asp Pro Leu Asp Pro
865                 870                 875                 880 cgt agc aac agc agc ctg gtg agg gac cct gcc ttc tcg gcc agc ggc    2688
Arg Ser Asn Ser Ser Leu Val Arg Asp Pro Ala Phe Ser Ala Ser Gly
                885                 890                 895 cct gag gcc cag cgc tgg ctg ctg gca ctc tgt cac cgg gcc cgg aat    2736
Pro Glu Ala Gln Arg Trp Leu Leu Ala Leu Cys His Arg Ala Arg Asn
            900                 905                 910 cag agc ttc ttc gac acc ctg cag gaa ggc tgg ccc acg ctg tgt ttc    2784
Gln Ser Phe Phe Asp Thr Leu Gln Glu Gly Trp Pro Thr Leu Cys Phe
        915                 920                 925 gtg gag acc ctc cag cgc tgg atg gag agc ccc agc tgc gcc cgc ctg    2832
Val Glu Thr Leu Gln Arg Trp Met Glu Ser Pro Ser Cys Ala Arg Leu
    930                 935                 940 ggg cct gac ctc tgc tgc ggc cac tcg gac ttc ccc tgg gcc ccc cag    2880
Gly Pro Asp Leu Cys Cys Gly His Ser Asp Phe Pro Trp Ala Pro Gln
945                 950                 955                 960 ttt ttc ctg cac tgc ctg aaa atg atg gct ctg gag caa ggc ccc gat    2928
Phe Phe Leu His Cys Leu Lys Met Met Ala Leu Glu Gln Gly Pro Asp
                965                 970                 975 ggc acc cag gac ctg gga ctc cgc ttt gat gcc cat ggc agc ctg gcc    2976
Gly Thr Gln Asp Leu Gly Leu Arg Phe Asp Ala His Gly Ser Leu Ala
            980                 985                 990 gcc ctg gtc cta caa ttc cag acc aac ttc cgg aac agt ccg gac tac    3024
Ala Leu Val Leu Gln Phe Gln Thr Asn Phe Arg Asn Ser Pro Asp Tyr
        995                 1000                1005 aac cag acc cag ctc ttc tac aat gag gtc agc cac tgg ctg gca gcg    3072
Asn Gln Thr Gln Leu Phe Tyr Asn Glu Val Ser His Trp Leu Ala Ala
    1010                1015                1020 gag ctg ggc atg gca cct cca ggc ctc cgc cgt ggt tgg ttc act agc    3120
Glu Leu Gly Met Ala Pro Pro Gly Leu Arg Arg Gly Trp Phe Thr Ser
1025                1030                1035                1040 cgt cta gag ctg tat agc ctg cag cac agc ctg agc act gag cct gct    3168
Arg Leu Glu Leu Tyr Ser Leu Gln His Ser Leu Ser Thr Glu Pro Ala
                1045                1050                1055 gtg gtg ctg ggc ctg gct ttg gcg ctg gcc ttt gcc aca ctg ctc ctg    3216
Val Val Leu Gly Leu Ala Leu Ala Leu Ala Phe Ala Thr Leu Leu Leu
            1060                1065                1070 ggc acc tgg aat gtt ccc ctc agc cta ttc tcc gtg gca gct gtg gca    3264
Gly Thr Trp Asn Val Pro Leu Ser Leu Phe Ser Val Ala Ala Val Ala
        1075                1080                1085 ggc acc gtg ctg ctc act gta gga ctc ctg gtt ctc ctc gag tgg cag    3312
Gly Thr Val Leu Leu Thr Val Gly Leu Leu Val Leu Leu Glu Trp Gln
    1090                1095                1100 ctc aac act gcc gag gcc ctg ttt ctc tct gcc tca gtg ggc ctc tca    3360
Leu Asn Thr Ala Glu Ala Leu Phe Leu Ser Ala Ser Val Gly Leu Ser
1105                1110                1115                1120 gta gac ttc act gtc aac tac tgc atc tcc tat cac ctg tgc cca cac    3408
Val Asp Phe Thr Val Asn Tyr Cys Ile Ser Tyr His Leu Cys Pro His
                1125                1130                1135
```

```
cct gac cgc ctg agc cgt gtg gcc ttc tct ctg cgc cag acc agc tgc     3456
Pro Asp Arg Leu Ser Arg Val Ala Phe Ser Leu Arg Gln Thr Ser Cys
        1140                1145                1150 gcc aca gcc gtg ggg gct gca gcc ctg ttt gcg gca ggc gtg ctc atg     3504
Ala Thr Ala Val Gly Ala Ala Ala Leu Phe Ala Ala Gly Val Leu Met
    1155                1160                1165 ctg cct gcc aca gtg ctg ctc tat cgc aag ctg ggc atc atc ctc atg     3552
Leu Pro Ala Thr Val Leu Leu Tyr Arg Lys Leu Gly Ile Ile Leu Met
        1170                1175                1180 atg gtc aaa tgc gtc agt tgt ggc ttt gcc agc ttc ttc ttc caa tct     3600
Met Val Lys Cys Val Ser Cys Gly Phe Ala Ser Phe Phe Phe Gln Ser
1185                1190                1195                1200 ctc tgc tgt ttc ttc ggg cca gag aag aac tgt ggg cag atc ctc tgg     3648
Leu Cys Cys Phe Phe Gly Pro Glu Lys Asn Cys Gly Gln Ile Leu Trp
        1205                1210                1215 ccc tgt gcc cac ctg cca tgg gat gct ggt act ggg gac cct ggt ggg     3696
Pro Cys Ala His Leu Pro Trp Asp Ala Gly Thr Gly Asp Pro Gly Gly
    1220                1225                1230 gag aag gca ggc cgc cca cga cca ggg tca gtg gga ggg atg ccc ggg     3744
Glu Lys Ala Gly Arg Pro Arg Pro Gly Ser Val Gly Gly Met Pro Gly
        1235                1240                1245 tcc tgc tca gag caa tat gag cta cag ccc ctg gca cgg cgt cgg agc     3792
Ser Cys Ser Glu Gln Tyr Glu Leu Gln Pro Leu Ala Arg Arg Arg Ser
    1250                1255                1260 ccc agc ttt gac acc agc aca gcc acc agc aag ctg tcc cac cgg ccc     3840
Pro Ser Phe Asp Thr Ser Thr Ala Thr Ser Lys Leu Ser His Arg Pro
1265                1270                1275                1280 tca gta ctc tct gag gat ctg cag ctc cat gat ggt ccg tgc tgt tcc     3888
Ser Val Leu Ser Glu Asp Leu Gln Leu His Asp Gly Pro Cys Cys Ser
        1285                1290                1295 cgg ccc cca cca gcc cct gcc tcc cca agg gag ctg ctg ctg gac cac     3936
Arg Pro Pro Pro Ala Pro Ala Ser Pro Arg Glu Leu Leu Leu Asp His
    1300                1305                1310 cag gca gtc ttc agc cag tgc cct gcc ctg cag acc tcc tcc ccc tat     3984
Gln Ala Val Phe Ser Gln Cys Pro Ala Leu Gln Thr Ser Ser Pro Tyr
        1315                1320                1325 aag cag gct ggc ccc agc ccc aaa acc cgg gcc agg cag gac tcc caa     4032
Lys Gln Ala Gly Pro Ser Pro Lys Thr Arg Ala Arg Gln Asp Ser Gln
    1330                1335                1340 ggg gag gag gct gag ccc ctg cca gcc tca cca gaa gcc cca gcc cac     4080
Gly Glu Glu Ala Glu Pro Leu Pro Ala Ser Pro Glu Ala Pro Ala His
1345                1350                1355                1360 tct cct aag gcc aag gct gca gat cct cct gat ggc ttc tgt tcc tca     4128
Ser Pro Lys Ala Lys Ala Ala Asp Pro Pro Asp Gly Phe Cys Ser Ser
        1365                1370                1375 gcc agc acc ctg gag ggg ctc agc gtc tct gat gag acc tgc cta agc     4176
Ala Ser Thr Leu Glu Gly Leu Ser Val Ser Asp Glu Thr Cys Leu Ser
    1380                1385                1390 acc tct gag ccc agt gcc cgt gta cca gat tcc gtg ggt gtg tcc cca     4224
Thr Ser Glu Pro Ser Ala Arg Val Pro Asp Ser Val Gly Val Ser Pro
        1395                1400                1405 gat gac ctg gat gac act ggg cag cca gtc ctt gag cga ggc cag ctc     4272
Asp Asp Leu Asp Asp Thr Gly Gln Pro Val Leu Glu Arg Gly Gln Leu
    1410                1415                1420 aat ggg aag cgg gac acc ctg tgg ctg gcg ctg agg gag aca gtg tat     4320
Asn Gly Lys Arg Asp Thr Leu Trp Leu Ala Leu Arg Glu Thr Val Tyr
1425                1430                1435                1440 gac cca tca ttg ccc gct tcc cat cac agc agc ttg tcc tgg aag ggc     4368
Asp Pro Ser Leu Pro Ala Ser His His Ser Ser Leu Ser Trp Lys Gly
        1445                1450                1455
```

-continued

```
cga ggg ggg cca ggg gat ggc agc cct gtg gtg ctg ccc aat agc cag    4416
Arg Gly Gly Pro Gly Asp Gly Ser Pro Val Val Leu Pro Asn Ser Gln
            1460                1465                1470 cca gac ctg cca gat gtt tgg ctg cgc agg ccc agc act cac acg tca    4464
Pro Asp Leu Pro Asp Val Trp Leu Arg Arg Pro Ser Thr His Thr Ser
        1475                1480                1485 ggc tat agc agc tga                                                 4479
Gly Tyr Ser Ser
    1490

<210> SEQ ID NO 3
<211> LENGTH: 44
<212> TYPE: DNA
<213> ORGANISM: Artificial Sequence
<220> FEATURE:
<223> OTHER INFORMATION: Oligonucleotide primer

<400> SEQUENCE: 3
gactagttct agatcgcgag cggccgccct ttttttttt tttt                    44

<210> SEQ ID NO 4
<211> LENGTH: 20
<212> TYPE: DNA
<213> ORGANISM: Artificial Sequence
<220> FEATURE:
<223> OTHER INFORMATION: Primer 1742-3538

<400> SEQUENCE: 4
cagcactcac acgtcaggct                                              20

<210> SEQ ID NO 5
<211> LENGTH: 21
<212> TYPE: DNA
<213> ORGANISM: Artificial Sequence
<220> FEATURE:
<223> OTHER INFORMATION: Primer 1742-3658

<400> SEQUENCE: 5
agaaatacct tcgggctcca g                                            21
```